United States Patent
Naghavi et al.

(10) Patent No.: US 10,517,487 B2
(45) Date of Patent: Dec. 31, 2019

(54) METHODS AND APPARATUS FOR ASSESSING VASCULAR HEALTH

(71) Applicant: ENDOTHELIX, INC., Houston, TX (US)

(72) Inventors: Morteza Naghavi, Houston, TX (US); Albert Yen, Pearland, TX (US); David Panthagani, Houston, TX (US); Stephen Cleboski, Houston, TX (US); Haider Hassan, Houston, TX (US)

(73) Assignee: American Heart Technologies, LLC, Houston, TX (US)

( * ) Notice: Subject to any disclaimer, the term of this patent is extended or adjusted under 35 U.S.C. 154(b) by 426 days.

(21) Appl. No.: 14/377,249

(22) PCT Filed: Mar. 25, 2014

(86) PCT No.: PCT/US2014/031672
§ 371 (c)(1),
(2) Date: Aug. 7, 2014

(87) PCT Pub. No.: WO2015/147796
PCT Pub. Date: Oct. 1, 2015

(65) Prior Publication Data
US 2016/0166157 A1 Jun. 16, 2016

(51) Int. Cl.
*A61B 5/02* (2006.01)
*A61B 5/01* (2006.01)
(Continued)

(52) U.S. Cl.
CPC ............ *A61B 5/02007* (2013.01); *A61B 5/01* (2013.01); *A61B 5/02055* (2013.01);
(Continued)

(58) Field of Classification Search
CPC .............. A61B 5/1455; A61B 5/02007; A61B 5/02028; A61B 5/02055; A61B 5/6826; A61B 5/7235
See application file for complete search history.

(56) References Cited

U.S. PATENT DOCUMENTS

2007/0173727 A1* 7/2007 Naghavi .................. A61B 5/01 600/483
2008/0255471 A1* 10/2008 Naghavi .................. A61B 5/01 600/549

\* cited by examiner

*Primary Examiner* — Christian Jang
(74) *Attorney, Agent, or Firm* — Frank Pham; Pham IP Group

(57) ABSTRACT

A method for digital thermal monitoring assessment of vascular function comprising a temporary arterial occlusion using a pneumatic cuff positioned on a subject's upper limb, monitoring skin temperature at the fingertip of the occluded limb for a period of time before, during, and after the occlusion, calculating a Zero Reactivity Curve based on variables including start temperature, room temperature, and the slope of temperature decline during the occlusion, and assessing vascular function based on comparing the Zero Reactivity Curve and the observed temperature rebound after the occlusion is removed. A vascular reactivity monitoring apparatus for measuring skin surface temperature comprising an inflatable cuff for placement around a subject's limb, a digital thermal measuring device and photoplethysmography measuring device for placement on a finger of the subject's limb wearing the cuff and a second digital monitoring device and photoplethysmography measuring device for placement on a finger of the subject's contralateral limb.

4 Claims, 25 Drawing Sheets

(51) Int. Cl.
*A61B 5/0205* (2006.01)
*A61B 5/024* (2006.01)
*A61B 5/0402* (2006.01)
*A61B 5/1455* (2006.01)
*A61B 5/00* (2006.01)

(52) U.S. Cl.
CPC ........ *A61B 5/02405* (2013.01); *A61B 5/0402* (2013.01); *A61B 5/14551* (2013.01); *A61B 5/6826* (2013.01); *A61B 5/7275* (2013.01)

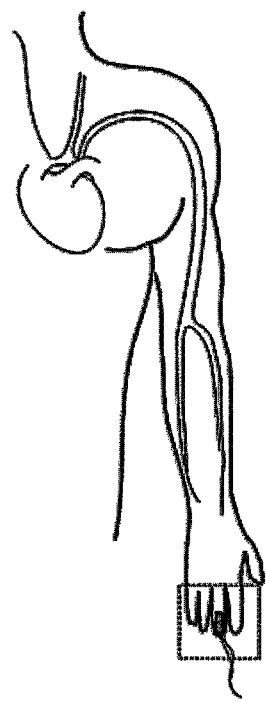 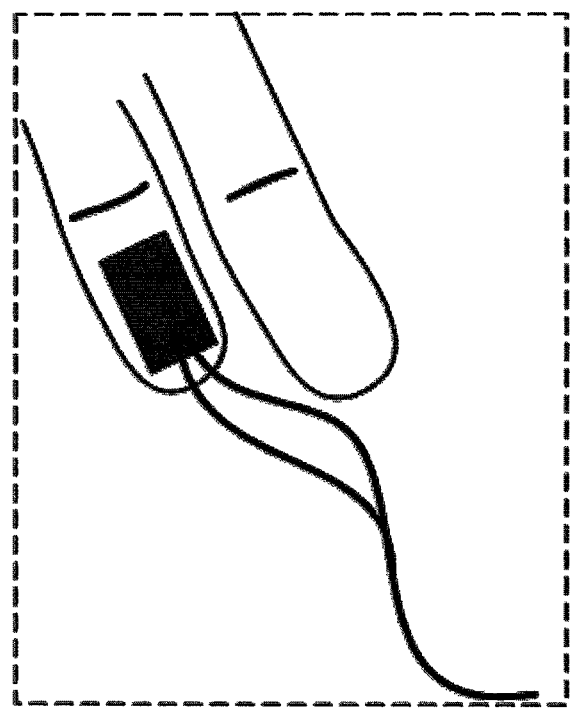
FIGURE 9a.  FIGURE 9b.
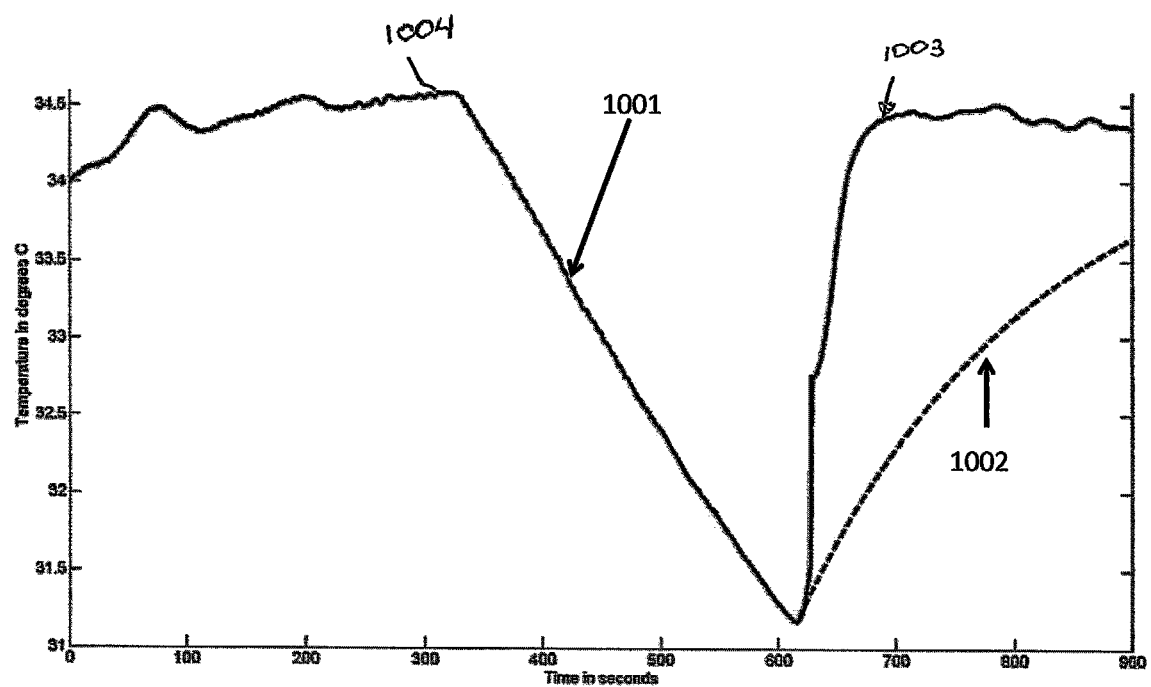
Figure 10

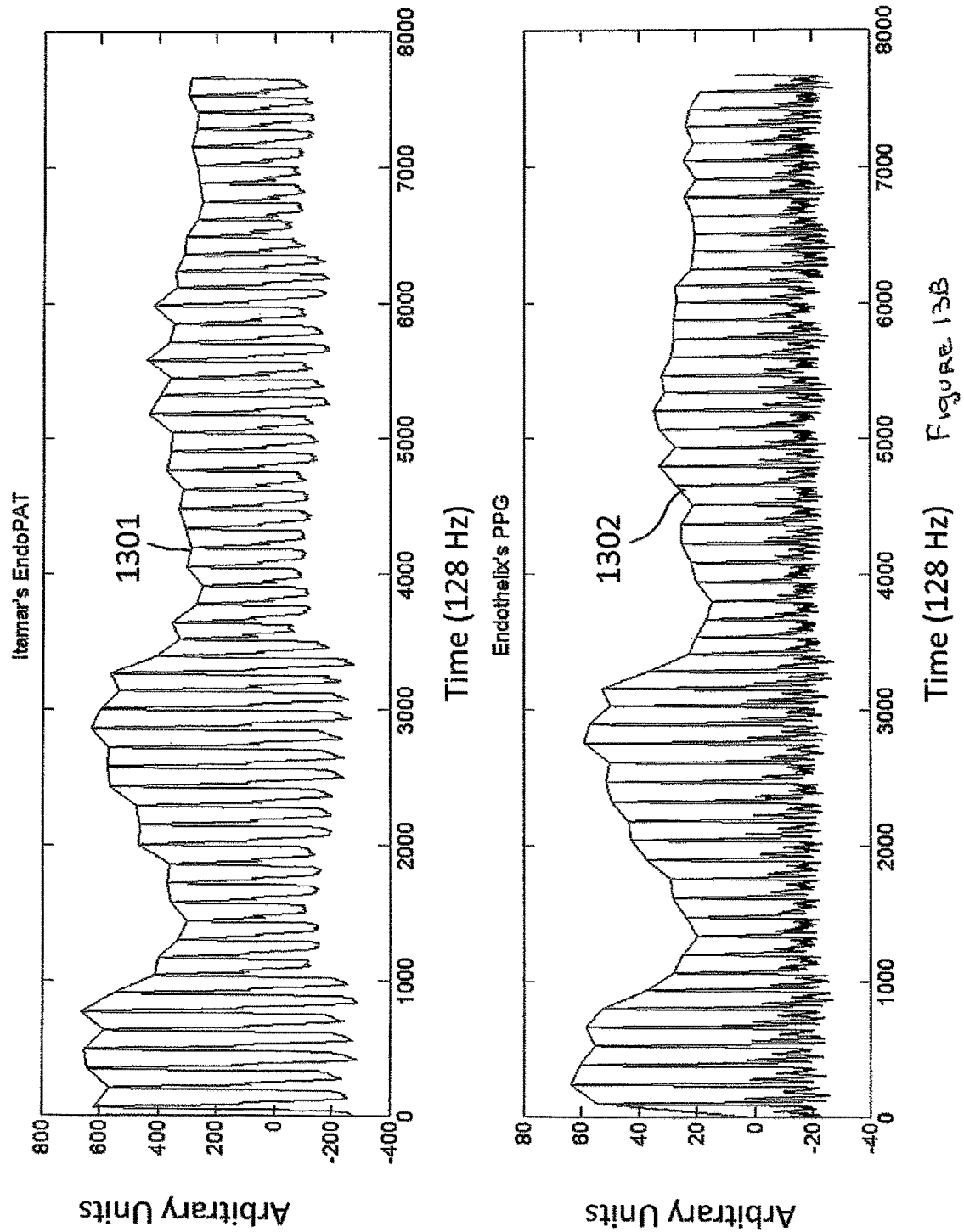

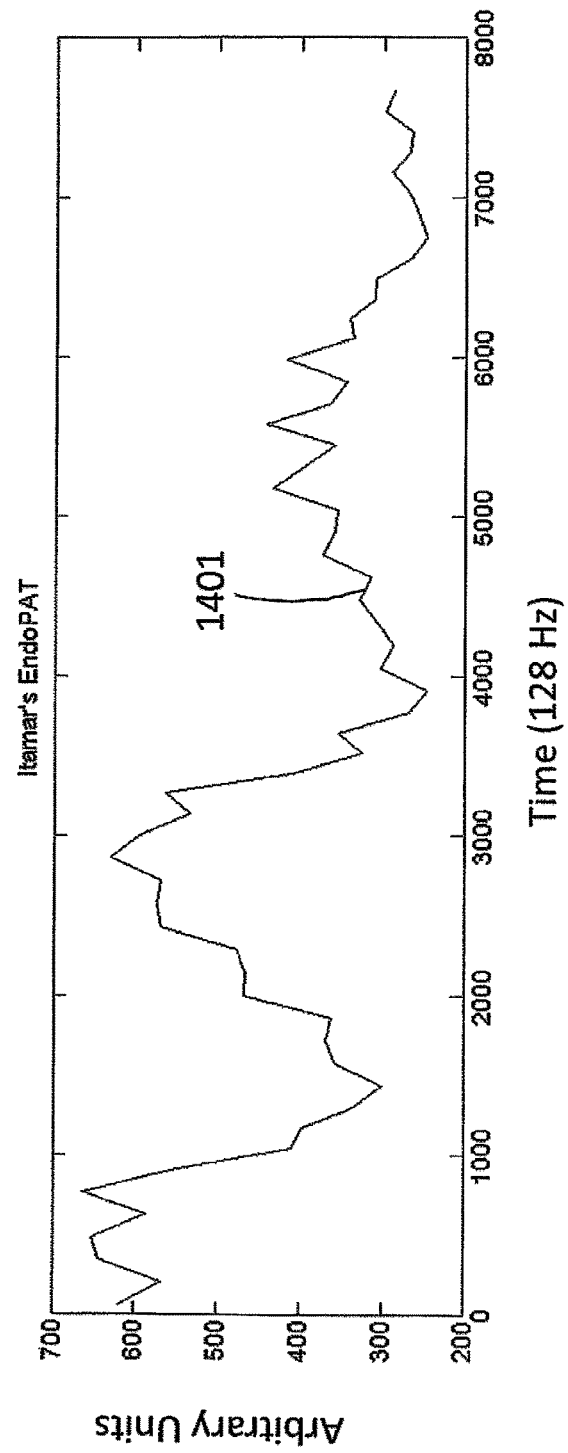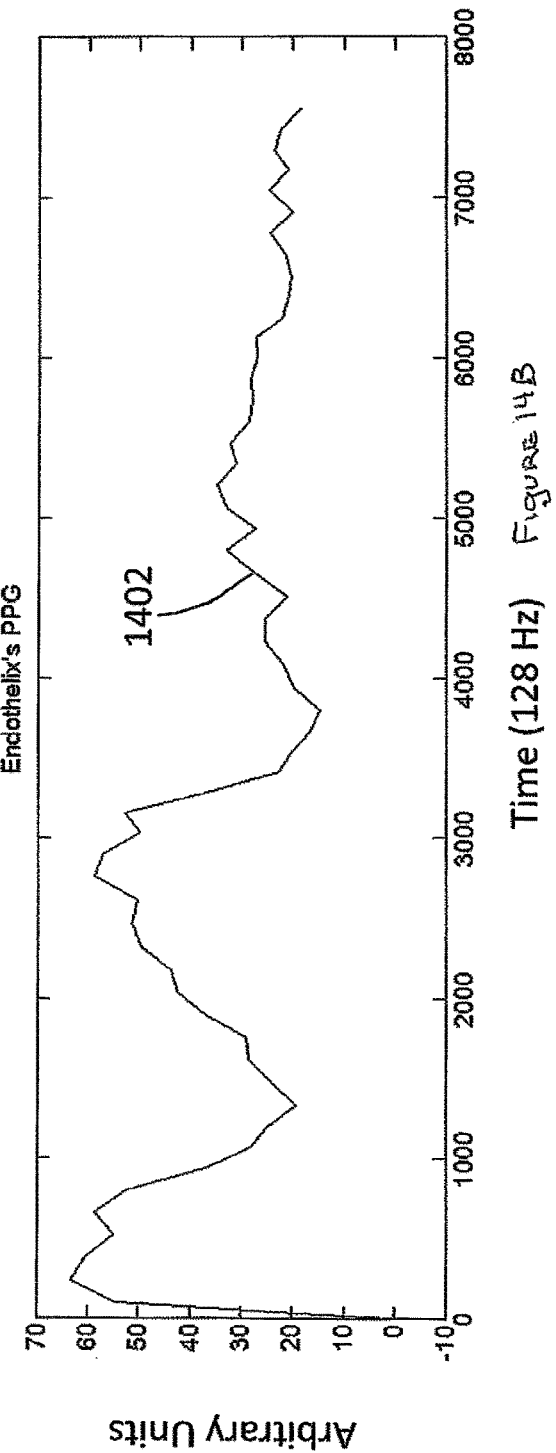
Figure 14A Itamar's EndoPAT
Figure 14B Endothelix's PPG

METHODS AND APPARATUS FOR ASSESSING VASCULAR HEALTH

RELATED APPLICATION

This application claims priority to pending PCT application No. PCT/US2014/31672 filed Mar. 25, 2014. This application is being filed in compliance with 35 U.S.C. 371.

FIELD OF THE INVENTION

The present invention relates generally to the field of assessing a patient's vascular health.

BACKGROUND OF INVENTION

Variation in skin temperature resulting from a temporary vasostimulant such as a temporary occlusion of an artery in a limb has been studied. It is established that, properly conducted in the context of other variables, this study can provide valuable evidence of a subject's cardiovascular health by providing a quantitative measure of the subject's vascular function. The previously established method of assessing vascular function based on monitoring of fingertip (digital) skin temperature before, during, and after applying a temporary vasostimulant has been termed Digital Thermal Monitoring, or DTM. The inventors have automated the DTM test procedure, and this automation has eliminated the inter-operator variability that is commonly observed when DTM tests, and any other cuff reactive hyperemia tests, are performed manually by different operators. However, it was recognized that variability of test results due to environmental conditions and subject preparation can still exist. What is needed are additional ways of improving the reproducibility and technical quality of DTM tests, as well as ways of identifying the presence of specific subject and testing conditions that may influence the DTM test results.

SUMMARY OF DISCLOSURE

This disclosure relates to improving the Digital Thermal Monitoring, or DTM, method of assessing the vascular function of an individual. The DTM method involves creating a vasostimulant in a subject's limb while monitoring skin surface temperature near the tip of a subject's digit of the limb. One form of vasostimulation is the temporary occlusion of the blood supply to the limb of a subject. This disclosure will speak specifically of occluding the blood supply utilizing an inflatable cuff. This cuff can be similar to a blood pressure cuff or sphygmomanometer. It will be appreciated that other devices can be used. The key factor is the ability to controllably achieve and maintain suprasystolic pressure in the subject's limb with minimal discomfort. Although a cuff device can be used on a subject's leg, this disclosure will speak primarily of use of a cuff to achieve a temporary ischemic condition of a subject's upper arm. Hence this disclosure will speak of monitoring skin temperature near the tip of the finger of the arm subject of the temporary ischemic condition. Further, this disclosure will speak of the right arm being subject of the temporary ischemic condition. The left arm will be referred to as the contralateral arm or limb.

As has been previously described, the DTM method involves the monitoring and storing of fingertip skin temperature measurements in both right and left hands before, during, and after a temporary (5 minutes) cuff occlusion of the right arm. During the right arm cuff occlusion, temperature in the right finger will decrease. After the cuff is deflated, temperature in the right finger will typically increase, or "rebound." The rising temperature measurements in the right finger during the post-occlusion period are used to calculate a vascular reactivity index, which is a numerical score that quantifies the size of the vascular reactivity response. The higher the vascular reactivity index, the larger the vascular reactivity response, and hence, the better the vascular function.

This disclosure teaches an improvement on DTM-based vascular function assessment, one in which a Zero Reactivity Curve is calculated. Actual skin temperature measurements are compared to a calculated Zero Reactivity Curve. A vascular reactivity index that is adjusted based on Zero Reactivity Curve will help to control for varying room temperature, starting finger temperature, and size of subject's finger.

This disclosure also teaches methods of detecting subject or environmental conditions which may affect the technical quality of the DTM test or the calculated value of the DTM test result. These conditions will be referred to as Flagged Conditions. Examples of Flagged Conditions include Cold Finger, Sympathetic Response, Stabilization, Finger Room Delta, Cold Room, Fluctuating Room Temperature, Right versus Left, and Left Finger Drop.

Mathematical calculations are performed and algorithms are followed to determine when each Flagged Condition flag is triggered. By "trigger a flag," it is meant that all conditions required to satisfy that a Flagged Condition is present have been met.

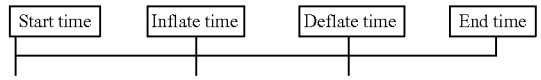

inflatetime=Time at which the cuff inflates (in seconds)
deflatetime=Time at which the cuff deflates (in seconds)
endtime=Time at which test ends (in seconds)
starttemp=Temperature of right finger at inflatetime
R=Temperature of Right Finger (finger of temporarily occluded arm)
L=Temperature of Left Finger (finger of contralateral arm)
Rm=Room temperature
maxR[t1:t2]=Maximum temperature of right finger from time point #1 to time point #2 (includes time points)
AVG(R[t1:t2])=Average of right finger temperature from time #1 to time #2 (includes time points)
R(inflatetime)=Temperature of right finger at inflatetime
Rm(inflatetime)=Temperature of room at inflatetime Cold Finger flag. This flag is triggered if the temperature of index finger of the occluded arm drops below 27° C. during the temperature stabilization period. Published literature and internal testing have indicated that a subject may be in a vasoconstrictive state if the finger temperature declines below 27° C. prior to the onset of cuff occlusion. A vasoconstrictive state is a condition where the arteries that supply the fingers with blood become narrowed, causing a reduction in blood flow to the skin surface of the fingers. This will cause the fingers to remain cold even after a period of occlusion and is likely to adversely affect the test results because the skin surface temperature may not accurately represent the underlying blood flow. If the Cold Finger flag is triggered during a DTM test, it is recommended that the test be halted prior to cuff occlusion and steps taken to warm the subject before trying the test again.

Sympathetic Response flag. Mental stress, bright lights, movement of other people, and physical discomfort are examples of factors which can elicit a state of increased sympathetic nervous activity in a subject whose vascular function is being assessed. The Sympathetic Response flag aims to detect the condition of excessive sympathetic nervous activity to an extent that it may adversely affect the technical quality of the calculated DTM test result. A sympathetic response will affect both the right finger temperature curve and the left finger temperature curve. Following the release of the cuff occlusion, the right finger temperature curve will not recover to the baseline measurement and may display a blunted or impaired temperature rebound in the presence of a sympathetic response; moreover, the left finger temperature curve will show a steady decline during the post-occlusion period. The algorithm for determining when this flag should be triggered is, as follows: After the cuff is deflated, the temperature of the right finger will start to recover. If the temperature of the right finger does not recover enough (to within 1 degree Celsius of the temperature at time of cuff inflation) and the linear slope (in degrees Celsius per second) of the left finger temperature from deflatetime to endtime is found to be decreasing sharply (less than −0.0067), then the Sympathetic Response flag should be triggered. If the Sympathetic Response flag has been triggered, it is recommended that the DTM test be repeated after efforts are made to relax the subject and remove any identifiable stressors or stimuli that could have provoked the sympathetic response.

Stabilization flag. This flag indicates that the left and right finger temperatures did not reach a stable value. Stability is defined as a relatively flat temperature curve in the last 3 minutes of stabilization phase. This flag can be cause by fluctuating room temperatures, excessive limb movement, or temperature probe detachment from the skin surface. The algorithm to detect stability consists of three consecutive checks, which are performed on the monitored finger temperature readings during the time period immediately preceding cuff occlusion: (1) The slope of the right finger temperature curve must be between −0.004 and 0.004 (in degrees Celsius per second) and the average right finger temperature must be above 27 degree Celsius. If either of these conditions fails, then the next check is run. (2) The right finger temperature curve should reach 31.5 degrees Celsius and the slope from the time point at which it reaches 31.5 C and inflatetime should be positive (greater than 0 C/sec). If either of these conditions fails, then the final check is run. (3) The right finger temperature curve should reach 31.5 degrees Celsius and the concavity of the temperature curve from the time point at which it reaches 31.5 C and inflatetime should be positive (greater than 0 C/sec$^2$).

Finger Room Delta flag. This flag indicates that the difference in finger temperature and the room temperature is too small to assess vascular function. If the difference between the right finger temperature and the room temperature is 3° C. or less, then the finger will temperature will not decrease sufficiently during the period of occlusion. This occurs in cases of unusually hot rooms or in cold finger scenarios.

Cold Room flag. This flag indicates that room temperature fell below 22° C. at some point during the test. A cold room can adversely affect the test by reducing the temperature of the patient and causing them to enter a vasoconstrictive state. Not every patient will be affected in this manner and many will complete the test with a valid result. In the case of an invalid test, however, this flag is used for evaluating the quality of the testing environment and identifying the source of the problem.

Fluctuating Room Temperature flag. This flag indicates that the room temperature has fluctuated more than 1° C. during the test. A varying temperature can be uncomfortable for the patient and adversely affect the test results.

Right versus Left flag. This flag indicates that the temperature difference between the left and right fingers during stabilization exceeds 3° C. This may indicate that the probe has moved or lost contact with the skin surface. This may also indicate that the test environment has uneven temperature distribution. For example, if one of the patient's hands was exposed to sun or a fan and the other was not, there will be a large difference in temperature between the hands. A large temperature difference can indicate that there is a problem with the testing environment that should be identified.

Comprehensive Assessment of Vascular Function by Simultaneously Measuring Microvascular and Macrovascular Reactivity.

This disclosure also teaches monitoring and measuring macrovascular and microvascular activity. In one embodiment, the disclosure teaches use of a photoplethysmogram to monitor macrovascular reactivity. This is considered to be a novel application of this device. It has been preferred practice to use Peripheral Arterial Tonometry (PAT) to measure macrovascular reactivity. PAT is a commercially available technology that primarily reflects a measure of macrovascular reactivity using pressure signal to measure net changes in blood volume at the fingertips, pre- and post-hyperemic response test (changes before and after a 5 minute cuff occlusion at the brachial artery accessed by positioning the cuff at the subject's upper arm). This disclosure also teaches use of Digital Thermal Monitoring (DTM) to simultaneously measure microvascular reactivity Digital Thermal Monitoring (VENDYS) is a commercially available technology to measure microvascular reactivity using temperature signal at the fingertips, pre- and post-hyperemic response test (changes before and after a 5 minute cuff occlusion at the brachial artery).

The combination of PAT and DTM is desirable to make both micro- and macro-vascular measurements but cannot be combined due to the following reasons:

PAT technology is highly sensitive to motion and therefore is a difficult measurement to make. PAT technology is also very costly and therefore not widely available.

This disclosure teaches utilizing a pulse-oximeter employing a photoplethysmogram (PPG). The PPG measurement can replace PAT measurement and produce the same results as the PAT test. In-house studies have yielded up to 96% correlation between PPG and PAT based vascular reactivity results implying that PPG is a good substitute for PAT.

A new technique of processing and analyzing the PPG signals has been developed that closely mimics PAT signals and can serve as a measurement of macrovascular reactivity. PPG technology does not interfere with the temperature measurements and can be easily combined with DTM to produce a single measurement apparatus that could measure both micro- and macro-vascular health at the same time. The advantage of the combination of PPG and DTM provides a single apparatus that can measure both macro- and micro-vascular health. The combination of the two indices can result in an improvement in the individual predictive value of either of the tests for detection of vascular dysfunction and thereby individuals at risk of a cardiovascular disease.

A PPG vascular reactivity index can be calculated using one or more of the following components derived from PPG signal analysis: peak to peak amplitude, peak to trough amplitude, pulse wave form analysis, area under the curve analysis, or reflectance waveform analysis.

Specifically, one aspect of the present disclosure is a method for determining one or more health conditions comprising providing a subject, measuring the skin temperature of a finger on the arm of the subject, detecting an equilibrium in the skin temperature of the finger of the subject, automatically providing a cuff occlusion to the subject to substantially cease blood flow to the finger, measuring the skin temperature changes of the finger after provision of the cuff occlusion, automatically removing the cuff occlusion to allow blood flow to the finger, measuring the skin temperature changes of the finger after the removal of the cuff occlusion, and measuring the subject's vascular reactivity. Vascular reactivity is the vasodilatory (widening) response of the blood vessels in the forearm and hand to a 5-minute period of cuff occlusion and tissue ischemia. The location of the occlusion can be the subject's upper arm.

In a preferred embodiment, based on the observed temperature fall in a finger of the subject's arm during the cuff occlusion phase and applying a novel variation of the Pennes thermal model of heat transfer, a zero reactivity curve (ZRC) is calculated and plotted as the expected temperature rebound curve if the test subject had zero vascular reactivity. In other words, if the blood vessels in the subject's forearm and hand (everything distal to the occluding blood pressure cuff) acted as if they were rigid pipes that cannot increase or decrease in diameter, then release of the cuff occlusion would result in a temperature rise in the right fingertip that would match the ZRC. In a further embodiment, the main index of vascular reactivity, the aTR (adjusted temperature rebound), is determined as the maximum (peak) difference between the observed temperature rebound curve and the calculated ZRC.

The maximum difference between the calculated ZRC and observed temperature rebound curve is assumed to result from warm blood flow into the forearm/hand that exceeds the amount that had been flowing before the cuff occlusion period. The term to describe this excess blood flow is reactive hyperemia. Reactive hyperemia is the transient increase in organ blood flow that occurs following a brief period of ischemia. Following ischaemia there will be a shortage of oxygen and a build-up of metabolic waste.

The present disclosure improves on the prior art by comparing the observed changes in fingertip temperature (microvasculature and microvasculature) with changes predicted by a model of zero vascular reactivity response.

The instant disclosure also teaches monitoring the fingertip temperature on the contralateral arm of the subject. As used herein for illustration, the right arm and index finger are subject of the temporary occlusion and the left arm and index finger is the contralateral limb.

Ultimately, this invention relates to new methods and apparatus for using digital (fingertip) thermal monitoring of vascular reactivity in ways which not been practiced before.

BRIEF SUMMARY OF THE DRAWINGS

The accompanying drawings, which are incorporated in and constitute a part of the specification, illustrate preferred embodiments of the disclosure. These drawings, together with the general description of the invention given above and the detailed description of the preferred embodiments given below, serve to explain the principles of the disclosure.

FIGS. 9a and 9b illustrate the PPG and single lead ECG sensor combined into one sensor.

FIG. 10 depicts a temperature curve of the right finger (1001) measured by DTM and the corresponding zero reactivity curve ZRC (1002) calculated from the temperature data.

FIGS. 13A and 13B is a comparison of raw PPG data and raw PAT data in a 1-minute interval. PPG is shown by the top graph (FIG. 13A) and PAT is shown in the bottom (FIG. 13B) PPG and PAT data were obtained concurrently from fingertip sensors positioned on two adjacent finger digits.

FIGS. 14A and 14B illustrates the primary area of comparison as the peak data of both signals. Using peak data, envelopes of the signals were generated and compared. PPG data (FIG. 2) and EndoPAT (FIG. 1) data were obtained concurrently from fingertip sensors positioned on two adjacent finger digits.

DETAILED DESCRIPTION OF THE DISCLOSURE

Figure 1:
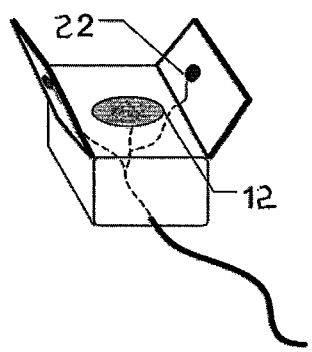
FIG. 1 depicts an embodiment of the finger probe which houses one temperature sensor [1] and one pulse oximetry sensor [2]. The pulse oximeter can be either a transmission or reflectance based probe. This embodiment shows a design that incorporates a transmission probe where the illumination source is located on one side of the probe body and the receiver is located on the opposite side.

This disclosure relates to improving the Digital Thermal Monitoring, or DTM, method of assessing the vascular function of an individual.

Digital Thermal Monitoring (DTM):

Certain of the present inventors have developed novel methods and apparatus to determine the vascular reactivity based on a measured response of the vasculature to reactive hyperemia utilizing continuous skin monitoring of inherent temperature on a digit distal (downstream) to an occluded arterial flow. By inherent temperature it is meant the unmodified temperature of the skin as opposed to measurement of the dissipation of induced temperature. This principal and technique has been termed Digital Thermal Monitoring (DTM). See commonly assigned WO 05/18516 and U.S. Pat. No. 8,551,008, the disclosures of which are incorporated herein by reference in their entirety.

It is well known that tissue temperature is a direct result of blood perfusion, but other parameters also contribute. These parameters can be classified as:

Anthropometric factors, such as tissue composition, skin thickness, fat content, surface area, tissue volume, body mass index, age and gender, among others.

Environmental factors, ambient temperature, the presence of air currents, unequal radiation, air humidity and posture.

Hemodynamic factors, due to the presence of large proximal conduit arteries and small vessels and capillaries, which respond differently to occlusion and reperfusion, and have different contributions to tissue temperature.

Physiological factors, i.e. body temperature, skin temperature, tissue metabolism, response of conduit vessel diameter to hypoxia and ischemia, microvasculature response, and the activation of arteriovenous anastomoses.

DTM is typically implemented by measuring temperature changes at the fingertips during reactive hyperemia induced by transient arm-cuff occlusion and subsequent release. The DTM probe does not transfer heat to the skin or tissue of the fingertip. It also does not place pressure on the fingertip. Adhesive devices are used to hold the DTM probe to the fingertip.

A normal reactive hyperemia response, i.e. increased blood flow after occlusion, is manifest by increased skin temperature over the baseline temperature established prior to occlusion. See FIG. 10.

The DTM measuring device is preferably placed proximate to the tip of the subject's finger on the right arm. The temperature monitor does not exert or subject the subject's skin to pressure. The temperature monitor does not supply thermal energy or heat to the skin.

The DTM test has three phases: temperature stabilization, cuff occlusion period, and post cuff deflation phase. The goal of the test is to measure a subject's vascular reactivity, which is the vasodilatory (widening) response of the blood vessels in the forearm and hand to a 5-minute period of cuff occlusion and tissue ischemia.

The disclosure teaches creating a vasostimulant. In one embodiment, the vasostimulant can be the occluding inflatation of an inflatable cuff positioned on the upper right arm of the subject. It will be appreciated that this is the same arm containing a Digital Thermal Monitoring device. The inflation of the cuff can be controlled. The inflated cuff can achieve pressure exceeding the suprastolic pressure of the brachial artery within the right arm. The start time of the cuff inflation (inflatetime) can be measured. The time can be measured in seconds.

It will be appreciated that the start time and deflate time (time at which the cuff is deflated) can be controlled by a programmable CPU or microprocessor. The deflate time (deflatetime) can be measured in seconds. The duration of the start time and deflate time can be recorded. The test continues until a new equilibrium temperature is recorded by the Digital Thermal Monitoring device. At the end time (endtime) the Zero Reactivity Curve may be calculated. Also recorded temperature at the inflate time may be plotted and the recorded change in temperature (recorded at the finger tip by the Digital Thermal Monitor) can be plotted. It will be appreciated that this measurement continues during the duration of the cuff inflation (vasostimulant) and continues after cuff release until a new temperature equilibrium is recorded. The measurements are plotted. The plot can be compared to the Zero Reactivity Curve. The temperature at which the temperature is recorded at the finger (after equilibrium measured) is termed the start temp (starttemp). It will be appreciated that the start temp is co-incident with the inflate time.

Figure 16:
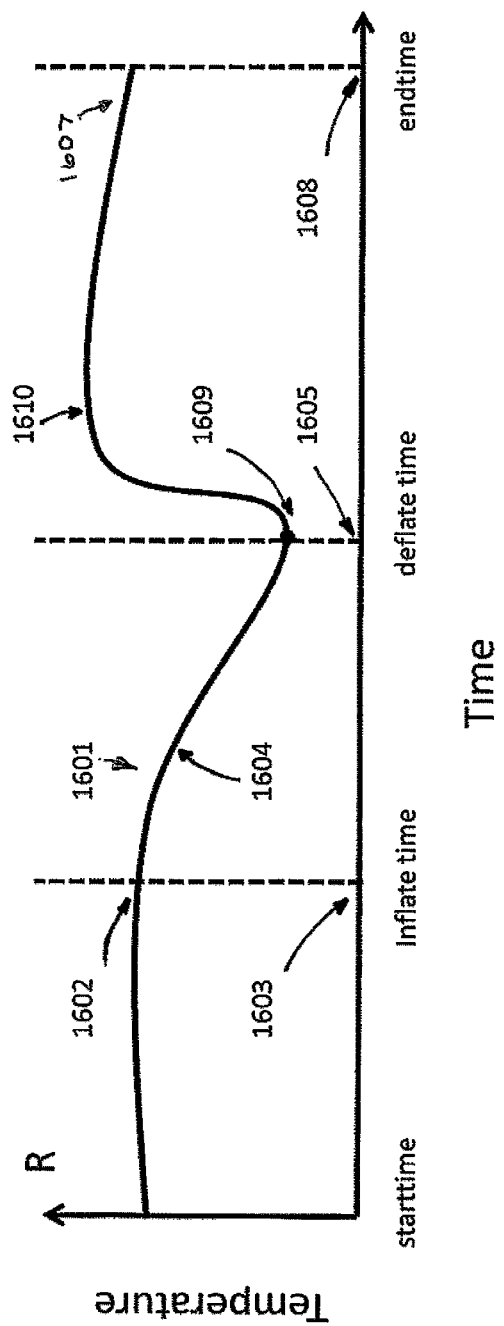
FIG. 16 plots a subject's skin temperature against time during which the subject's arm is temporarily occluded and subsequently released. The skin temperature falls during the time of occlusion and rebounds after the occlusion is removed. The temperature can be measured at a fingertip of the occluded arm utilizing DTM or a combination of DTM and PPG.

The plot of a typical measured DTM temperature curve incorporating a vasostimulant, measured by a Digital Thermal Monitoring device, is illustrated in FIG. 16. Different aspects or regions of the curve are studied and evaluated for different purposes. Temperature data for the left or contralateral arm can also be monitored and recorded during this time. The temperature of the contralateral arm may be used in validation of the test data. The curve is plotted by measured temperature against time. The curve (1601) shows an initial temperature stabilization (1602) at the inflate time (1603) followed by a decrease in temperature (1604) during the cuff occlusion period ending at a low temperature point or nadir 1609 at the deflate time (1605). The recorded temperature increases after the deflate time (1605). This is the post cuff occlusion period. Recall the deflate time is when the cuff inflation pressure is released and blood flow reperfuses through the brachial artery and the tissue of the arm. The temperature rebounds to a new maximum point 1610. Temperature is continued to be plotted until the endtime (1607) at which a new stabilization temperature (1608) is established.

The starttime begins and the skin temperature is monitored. The duration of the starttime period is approximately 5 minutes (300 seconds) at which time skin temperature has stabilized. The vasostimulant commences, e.g., the inflatable cuff on the subject's upper arm is inflated above suprasystolic pressure. The inflate time lasts approximately 5 minutes. During this time the temperature is continuously monitored at the fingertip using DTM. At the end of 5 minutes the cuff is deflated (deflate time) 1605. The blood reperfuses through the tissue of the arm including the fingertip monitored by the DTM. The temperature post occlusion period lasts 5 minutes to the endpoint 1608. The monitored temperature change in the arm caused by reperfusion can be compared to a Zero Reactivity Curve. The Zero Reactivity Curve is calculated using variables such as observed baseline temperature, the skin temperature at the fingertip at the beginning of the occlusion phase, and room temperature. The formula is discussed in detail below.

Figure 17A:
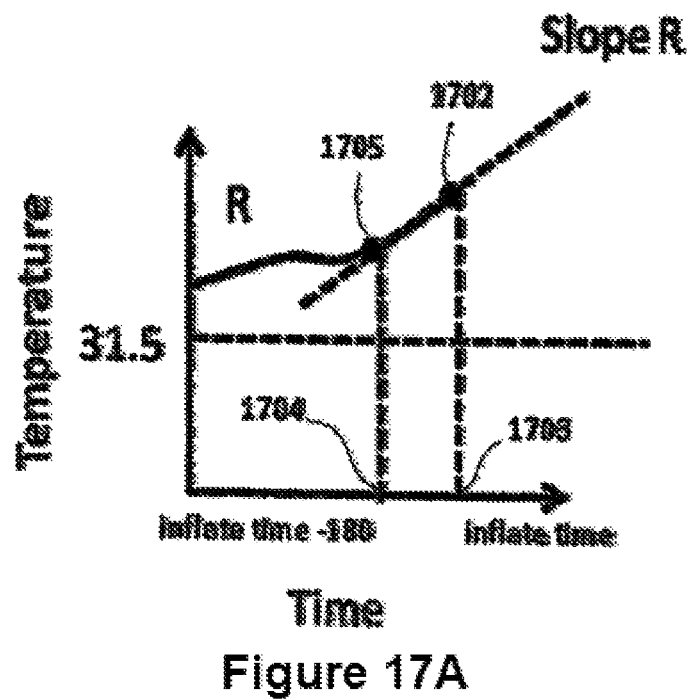
FIG. 17A is a plot of a subject's skin temperature plotted against time at a duration of time commencing 180 seconds before the start of the occlusion (inflate time).
Figure 17B:
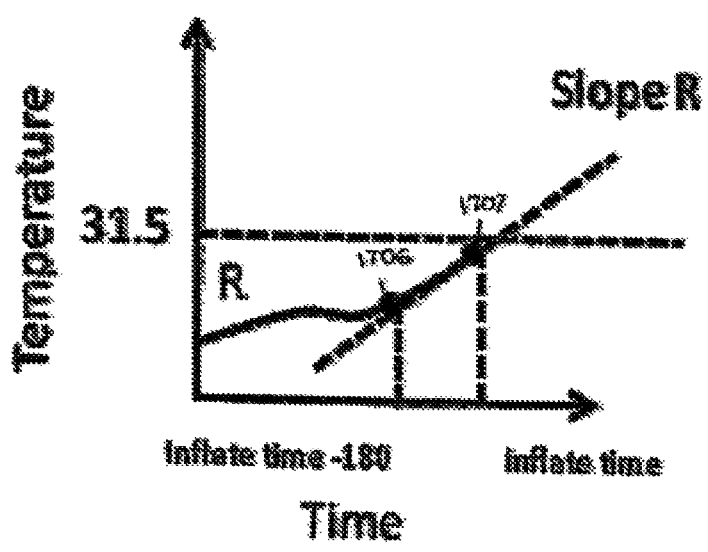
FIG. 17B is a similar plot but where the temperature is below 31.5° C.

The disclosure also teaches validation steps or "flags" before the occlusion begins. These validation steps can utilized monitored temperature data from the contralateral arm, assumed for this disclosure to be the left arm. FIG. 17A shows the plot of temperature change in the right arm (again, being understood to be the arm subject of the vasostimulant, e.g., occlusion by an inflatable cuff). This region of the temperature plot is used to check temperature stabilization. The graph plots the slope of the temperature change (Slope R) from 180 seconds prior to the inflate time (inflation of the inflatable cuff) 1704 to the time of inflation 1703. The temperature 1705 at the start of the 180 seconds is plotted. The temperature 1702 at the start of the inflate time is also plotted and the slope is computed. A determination is made whether the slope R is positive. The temperature 1702 at the inflate time is assessed. If the slope is positive and the temperature exceed 31.5° C., the Baseline Temperature Stabilization flag is deemed to be passed.

Figure 18:
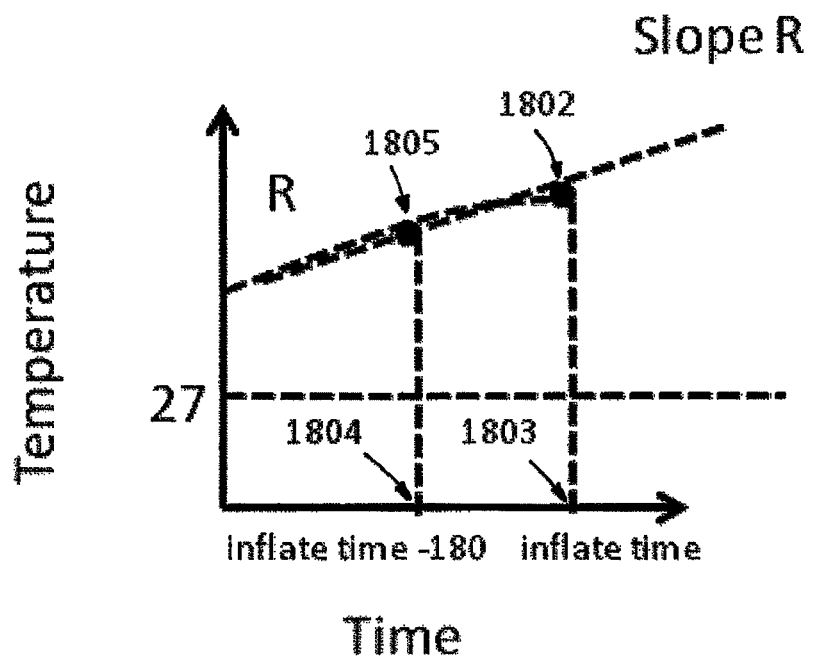
FIG. 18A is another plot of skin temperature wherein the period of interest is 180 seconds before the start of occlusion until inflation occurs (inflate time). The slope of the temperature change in calculated.
FIG. 18B illustrates another plot of skin temperature where the calculated slope is negative.
Figure 18B:
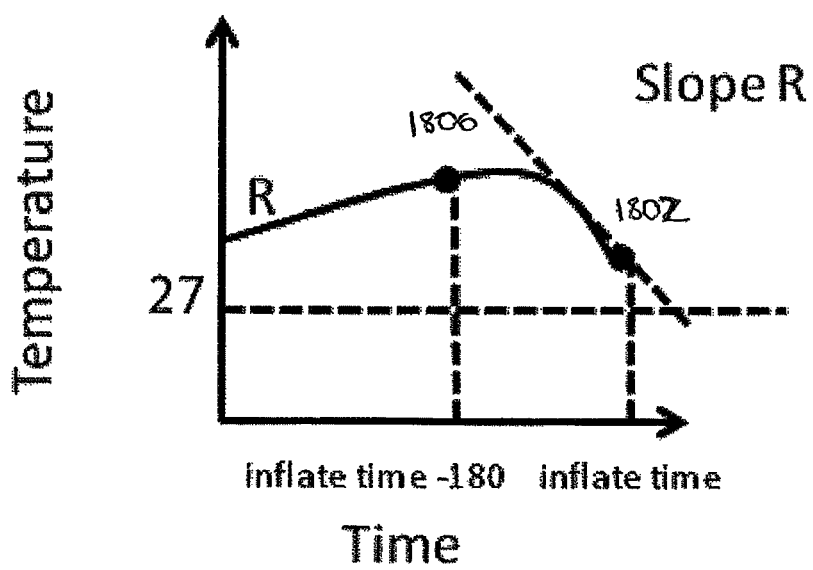

If the recorded temperature and time data does not reflect a positive slope or the recorded temperature is below 31.5 C, a second evaluation of the data is conducted. Again, the same portion of the temperature time curve is studied, i.e., the period between 180 seconds before the inflate time through to the inflate time. FIG. 18 illustrates an example of this evaluation (termed S.2). The temperature 1805 at the point 1804 being 180 seconds before the inflate time and the temperature 1802 at the inflate time 1803 are used to calculate a slope (Slope R). The slope is evaluated whether it is level or close to zero. The evaluation determines whether the slope satisfies the expression $0.004<\text{Slope R}<-0.004$. If the slope satisfies this expression and the recorded temperature at the inflate time (1802) exceeds 27° C., the Baseline Temperature Stabilization flag is deemed to be passed.

Figure 28:
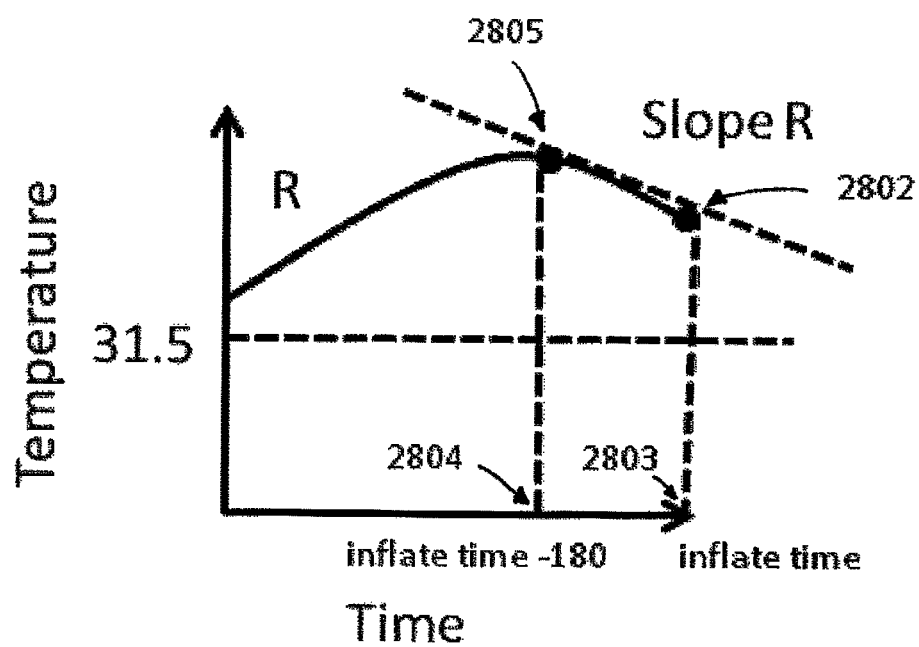
FIG. 28 illustrates the slope of the temperature change of the right arm from a point 180 seconds before the start of the cuff inflation (inflate time−180) and the time the cuff is inflated (inflate time).
Figure 29:
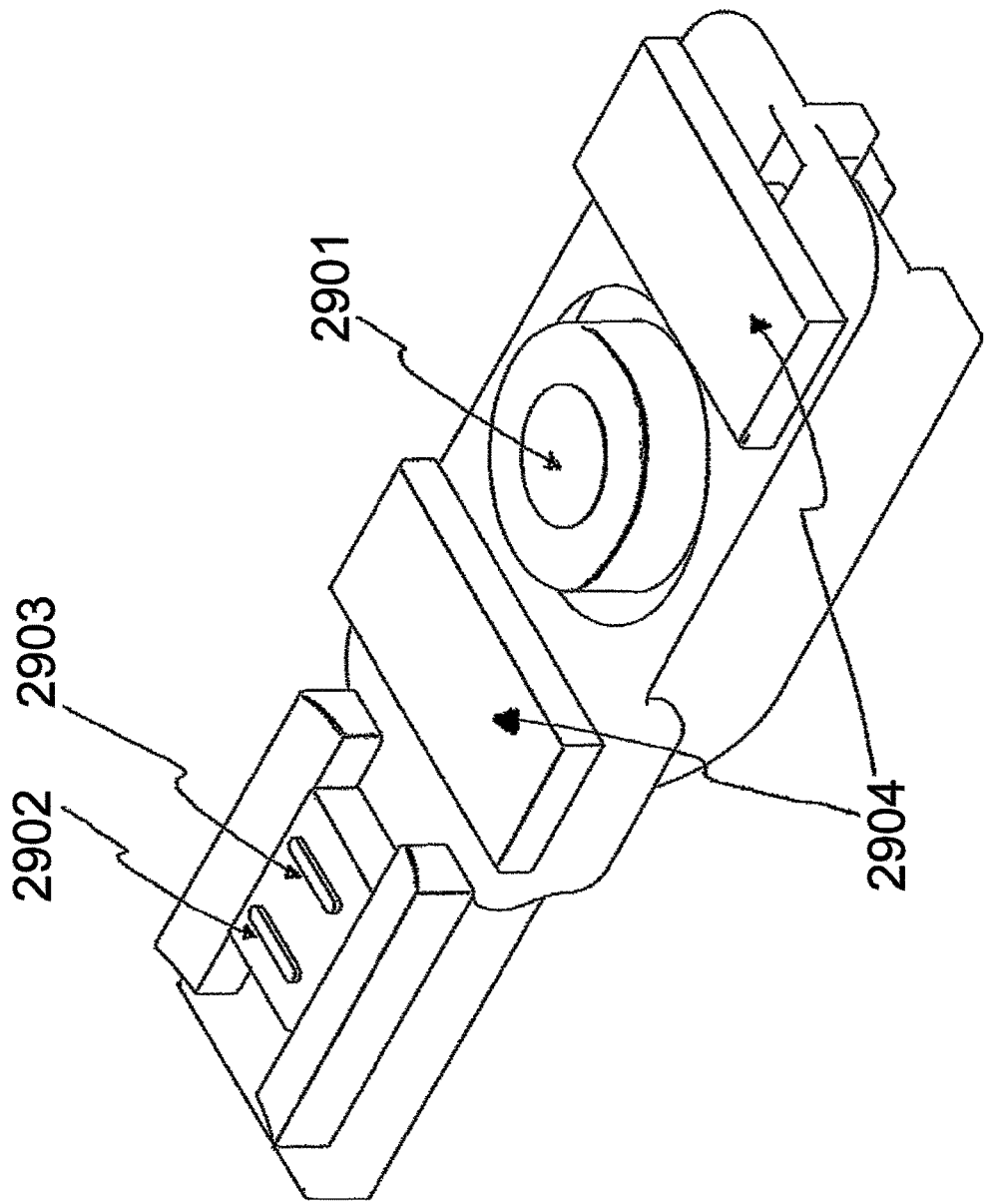
FIG. 29 illustrates a photoplethysmography (PPG) sensor. Illustrated is a temperature sensor. When in use, the sensor is pressed against the pulp of the fingertip. The sensor can be used on fingertips of both the subject's right and left hand. Also illustrated is LED component of the PPG. Also illustrated is a detector that absorbs light reflected off the subject's fingertip tissue. Also illustrated are adhesive pads to adhere the finger to the PPG sensor.

FIG. 28 illustrates an example where the evaluation S.2 is not passed. The temperature 2802 at the inflate time 2803 is greater than 31.5° C. However the slope of the line defined by the temperature 2805 at time 2804 (inflate time−180 seconds) and temperature 2802 at time 2803 (inflate time)

forms a slope R where slope R is negative. Therefore Baseline Temperature Stabilization flag S.2 is not passed.

Figure 19:
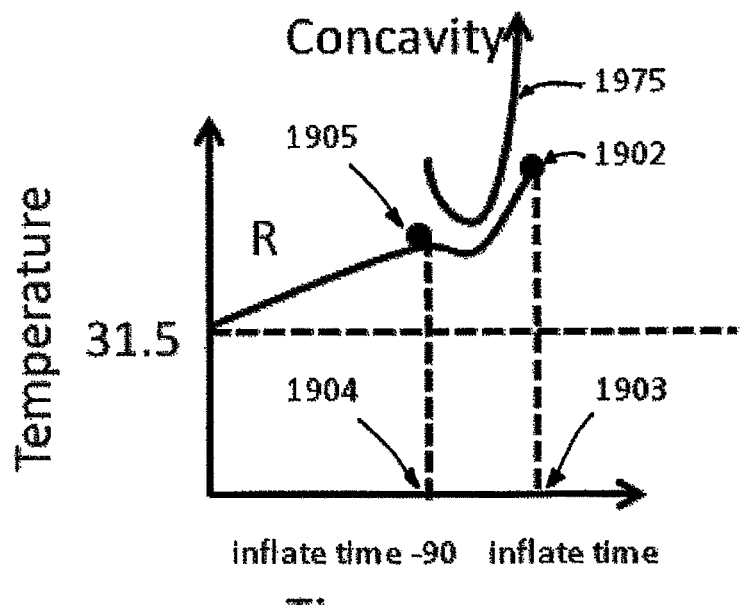
FIG. 19 is another plot of the change in a subject's skin temperature. The period of interest is the duration 90 seconds before inflate time until and including the start of inflation of the occluding cuff.
Figure 20:
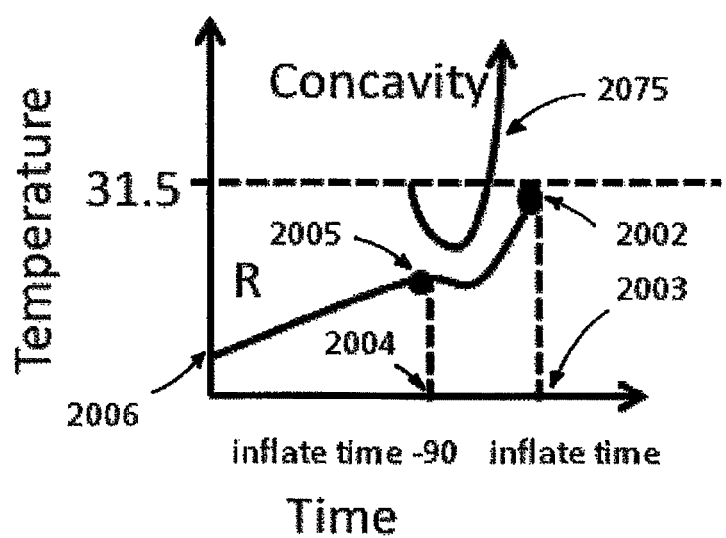
FIG. 20 is another plot of the change in the subject's skin temperature from 90 seconds before inflation time and including the start of inflation of the occluding cuff.

If the expression for the slope is not met or the temperature at the inflate point is not greater than 27° C., then a third evaluation is performed (designated S.3). FIG. 19 illustrates this evaluation and reviews the recorded data at the time 1905 90 seconds before the inflate time 1902. If recorded temperature between these two points forms an upward facing concave shape (as exhibited by vector arrow 1975) and the recorded temperature at the inflate time 1903 exceeds 31.5° C., the Baseline Temperature Stabilization flag is deemed to be passed. If this third evaluation is not passed, the test is deemed to be failed and must be restarted. This can be determined by a CPU or microprocessor. FIG. 20 illustrates a test that does not pass the S.3 criteria, i.e., the temperature 2002 at the inflation point is below 31.5° C. Also illustrated is the temperature at the start point 2006, the inflate time minus 90 seconds 2004, and the inflate time 2003.

Figure 21:
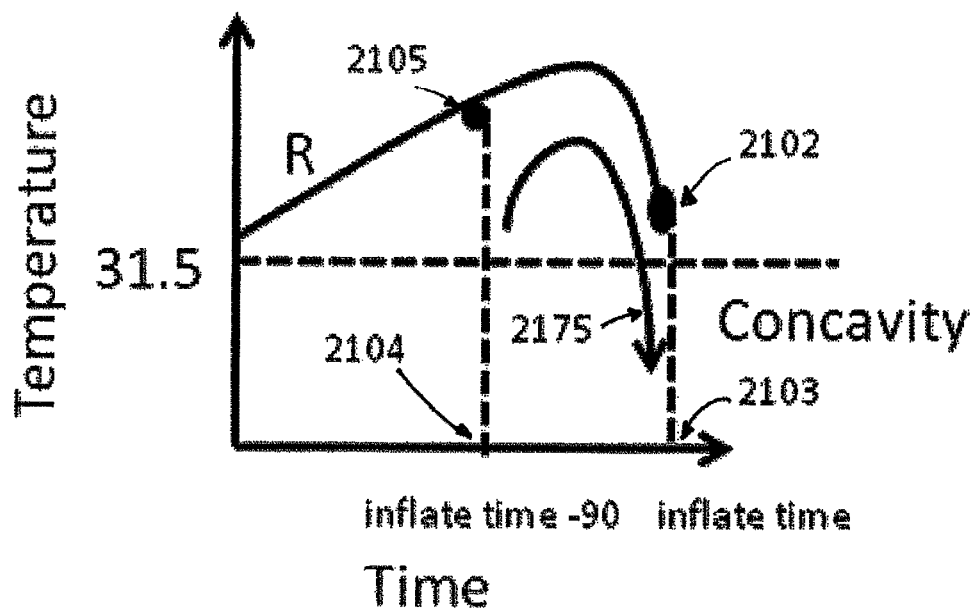
FIG. 21 is another plot of the change in the subject's skin temperature from 90 seconds before inflation time and including the start of inflation of the occluding cuff.

FIG. 21 illustrates a second example where the S.3 Baseline Temperature Stabilization flag is not passed. Note the shape of the vector arrow 2175 which illustrates the plot of the temperature 2105 between the time 2104 and the inflate time 2103 temperature 2102. The vector arrow 2175 forms a downward facing concave shape. The test is deemed to fail even though the temperature at the inflate time 2103 exceeds 31.5° C.

Figure 22:
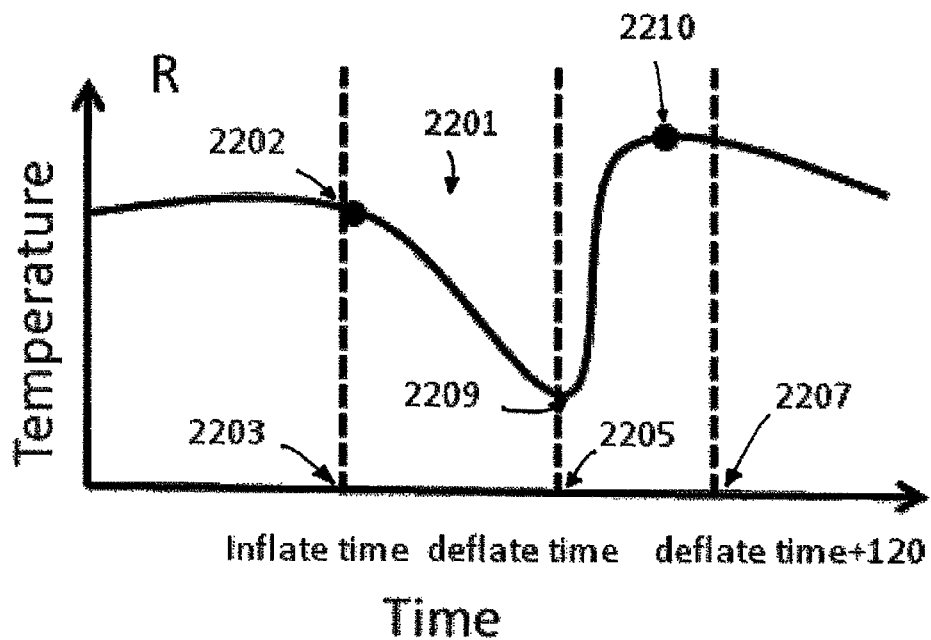
FIG. 22 is a plot of the change in a subject's skin temperature in the occluded arm. The temperature plot extends from 300 seconds prior to cuff inflation (inflate time) through the drop in skin temperature during occlusion and the nadir wherein the cuff is deflated. The plot shows the temperature rebound from blood reperfusion to a new maximum temperature and temperature stabilization.

FIG. 22 illustrates the temperature curve 2201 of the right arm measured by DTM proximate to the right hand fingertip. The skin temperature 2202 at the inflate time 2203 is noted and compared with the temperature maximum 2210 after the minimum temperature 2209 at the deflate time 2205. If the temperature of the right monitored finger does not recover to within 1 degree of the temperature at inflation, Δt greater than 1° C. then the slope of the left finger must be calculated. This is designated SR.1. It is a measure of the sympathetic nervous system response. FIG. 22 illustrates the rebound or recovery temperature 2210 exceeding the inflate time temperature 2202. The recovery temperature has clearly rebounded to within 1° C. See FIG. 24.

Figure 23:
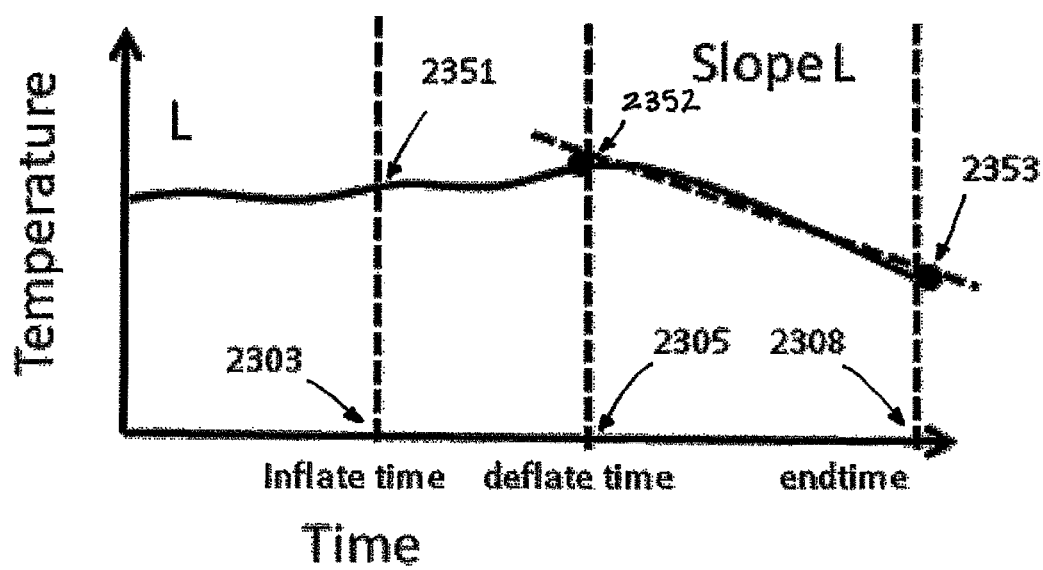
FIG. 23 illustrate the plot of the skin temperature in the left arm (non-occluding). The time period of interest is the skin temperature of the left arm from the time the cuff (right arm) is deflated until the end time (300 seconds after deflate time).
Figure 24:
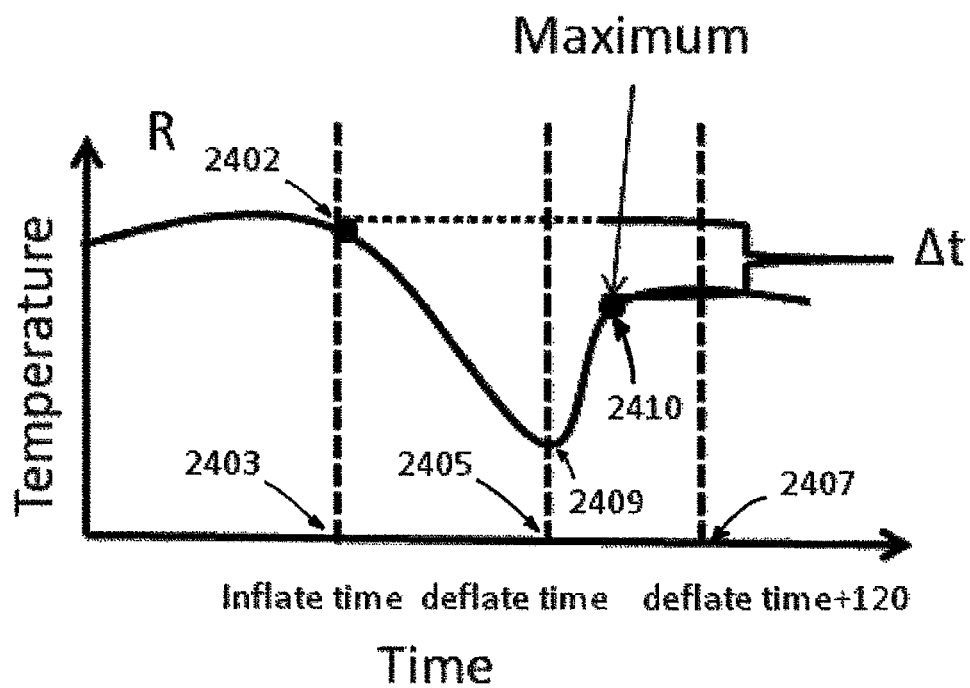
FIG. 24 is an illustration of the plot of skin temperature in the right arm (occluded) comparing the temperature at the point of occlusion (inflate time) through the nadir of the skin temperature drop (deflate time) and the new rebound temperature through 120 seconds after the cuff is deflated. The new temperature maximum (rebound maximum) is compared to the temperature at the start of occlusion.
Figure 25:
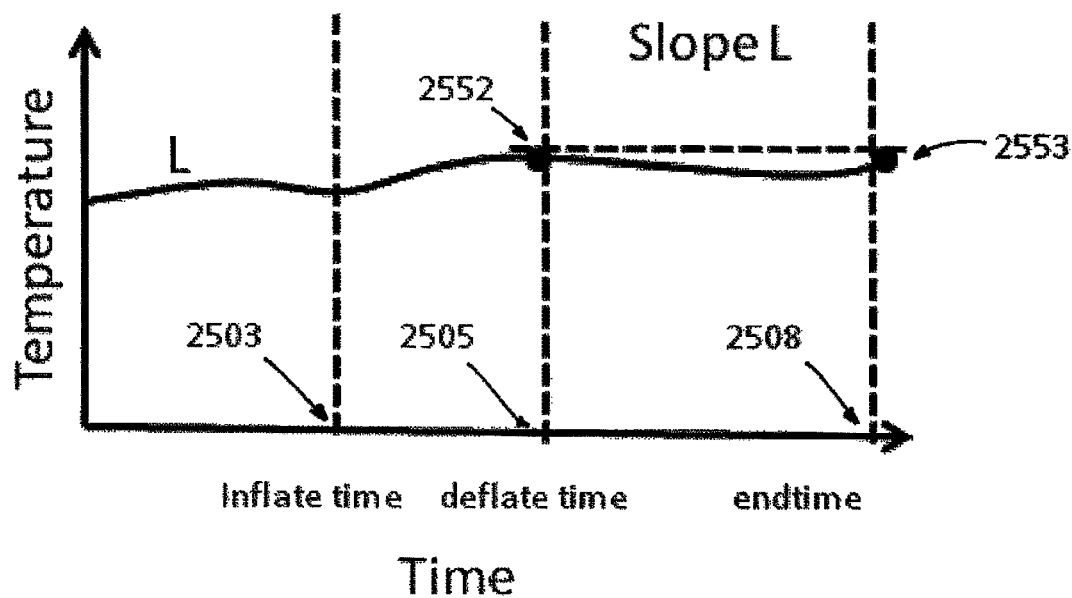
FIG. 25A is an illustration of the neurovascular reactivity of the left arm during the cuff inflation. The Figure also illustrates the continued temperature increase in the left arm after cuff deflation.
FIG. 25B illustrates DTM of Vascular Reactivity and Neurovascular Reactivity. The decrease in skin temperature of the right arm during occlusion with a simultaneous temperature rise in the left arm during this occlusion period.
Figure 25:
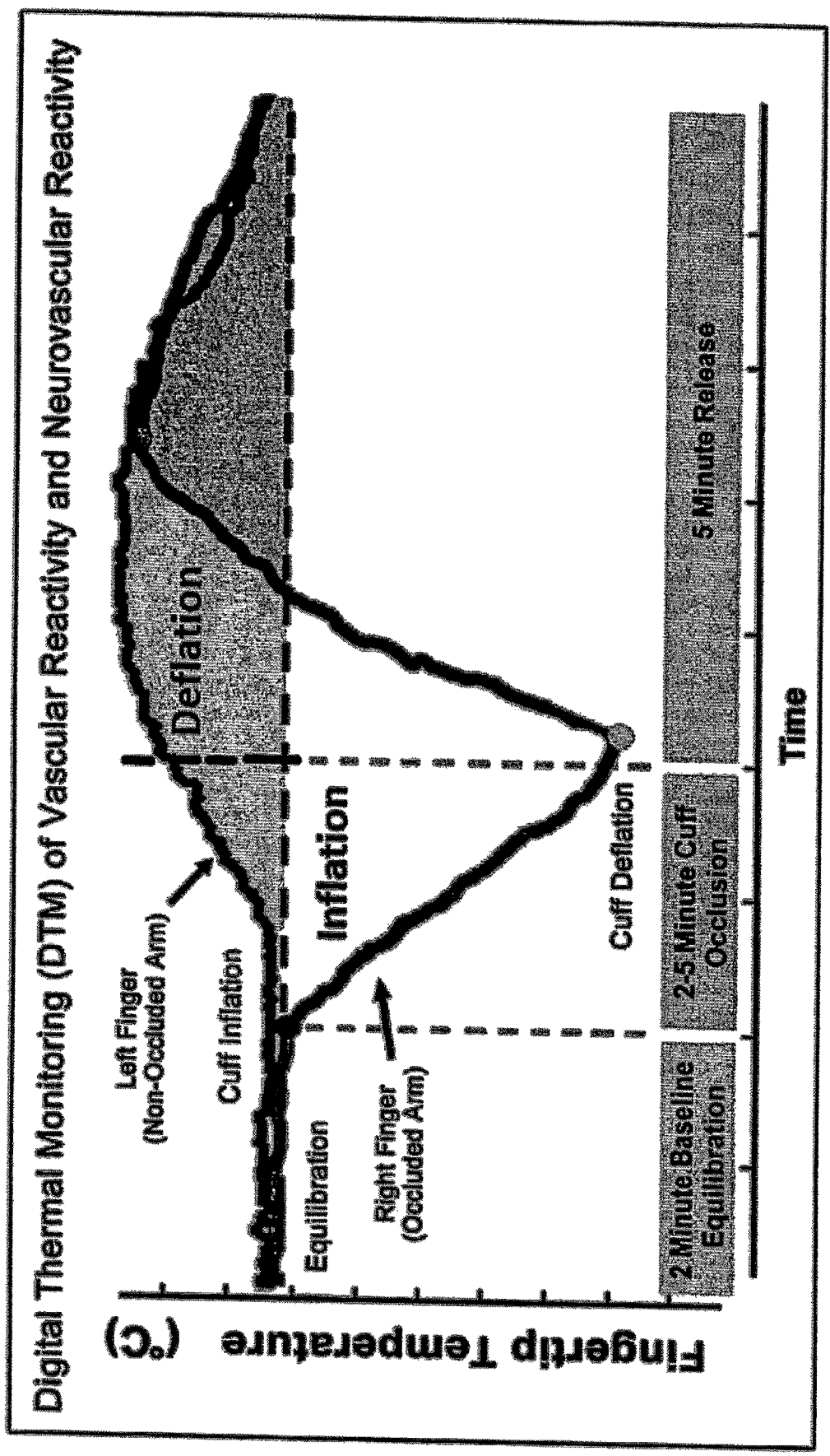
Figure 26:
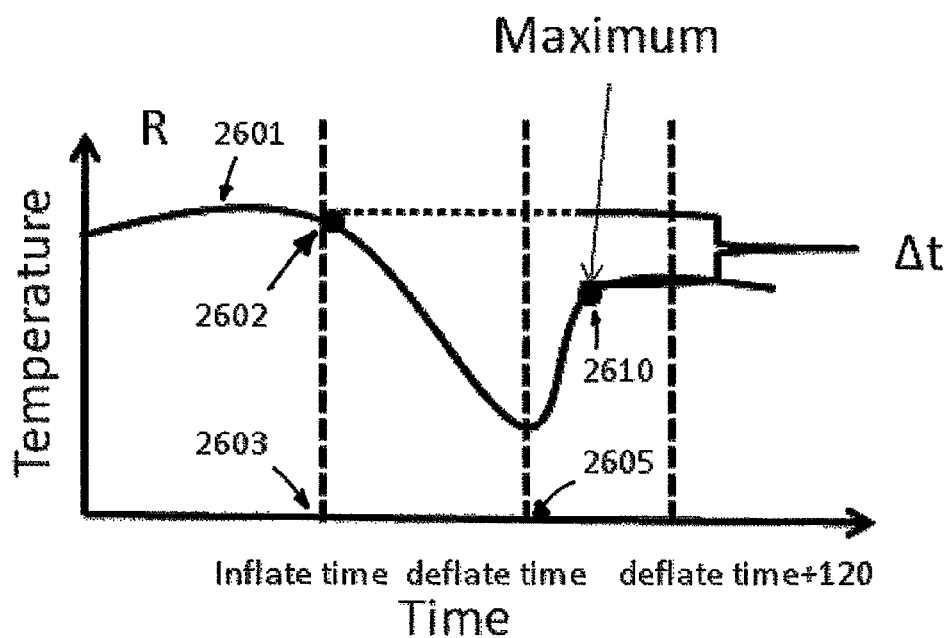
FIG. 26 is an illustration of the plot of temperature change in the right arm wherein the slope of the temperature change is computed from the time the cuff is deflated (deflation time) to a point 120 seconds after cuff deflation.

This event is illustrated in FIG. 24 wherein the difference between temperature 2402 at time 2403 (inflate time) and maximum recovery temperature 2410 after deflate time 2405 is greater than 1° C. Maximum temperature 2402−maximum recovery temperature 2410>1° C. In this event, the slope of the recorded temperature for the left hand must be evaluated as illustrated in FIG. 25. The recorded temperature, monitored by DTM proximate to a fingertip of the left hand, is evaluated from the deflate time 2505 and the end time 2508. Recall that the end time is 300 seconds after the deflate time. The slope of the line comprising temperature point 2552 and 2553 is calculated. If the slope is less than −0.00167, then the test (designated SR.2) is deemed to fail. In FIG. 26, the slope is greater than −0.00167 and the test is deemed to pass FIG. 23 illustrates an example where the measurement of the contralateral arm is used in the validation of a test. In this example, the slope of the temperature between the deflate time and the end time is calculated. Here, in this example, the slope of the recorded temperature of the left hand does not pass, i.e., the slope L is less than −0.00167. Slope L is formed by the temperature 2352 recorded at the deflate time 2305 and the temperature 2353 recorded at the end time 2308. Also illustrated is the temperature 2351 of the left hand at the inflate time 2303.

Figure 27:
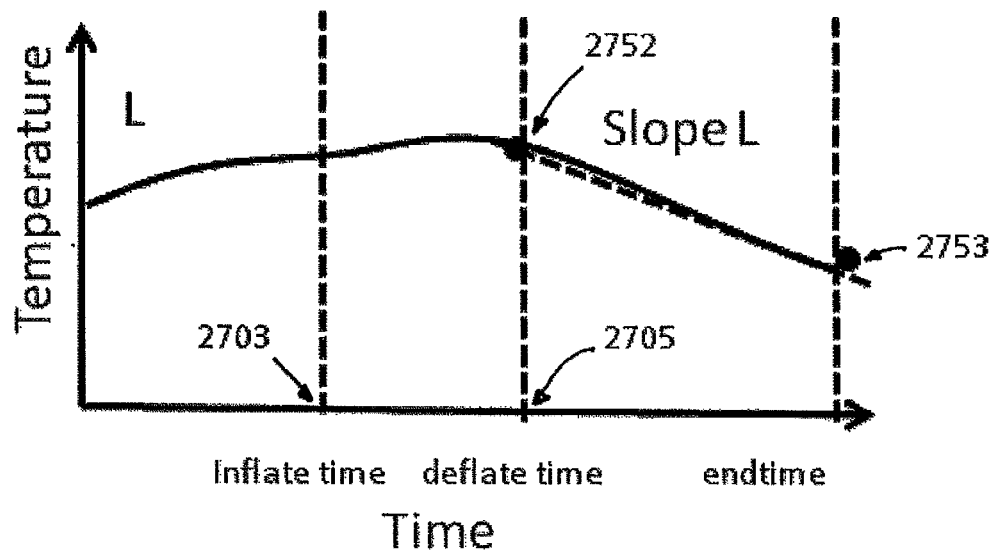
FIG. 27 is another plot of the temperature change in the left arm wherein the slope of the temperature change is computed from the time the cuff is deflated (deflation time) to a point 300 seconds after cuff deflation (end time).

This relationship is again illustrated in FIGS. 27 and 28. FIG. 27 illustrates the recorded temperature curve 2601 for the right hand (monitored by DTM proximate to a right hand finger tip). Illustrated is the temperature 2602 and the inflate time 2603. The maximum recovery temperature 2610 is also illustrated. It will be appreciated that this maximum recovery period occurs within the first 120 seconds after the deflate time 2605. At is illustrated to be greater than 1. Stated differently, the recovery temperature has not reached within 1° C. of the temperature 2605. This result requires evaluation of the slope of the left (non-occluded) arm. This evaluation is disclosed in FIG. 28. The slope is evaluated in the left arm temperature 2752 from the deflate time 2705 to the temperature 2753 at the end time. The slope is shown to be less than −0.0067. (Slope L>−0.00167). The test is deemed a failure. The test must be re-performed.

This disclosure also teaches the phenomena of the left arm (contralateral arm) experiencing increased blood flow and resulting increasing temperature in response to the occlusion of the artery in the right arm caused by cuff inflation. See FIG. 25. The temperature of the right finger of the occluded arm is shown to be decreasing after cuff inflation (on the right arm). The left (contralateral) arm experiences an increase in blood flow during the cuff inflation time and continuing during the cuff deflation time. Without being tied to theory, this reaction is viewed as an indicia of strong neurovascular reactivity. It will be appreciated that some subjects experience an apparent sympathetic neural reactivity wherein the blood flow in the left arm decreases contemporaneously with the occluded blood flow in the right arm.

This disclosure also teaches a novel indexing method for both individualized and comparative analysis of cardiovascular health based upon a predicted vascular reactivity curve. This predicted vascular reactivity curve is termed zero reactivity curve or ZRC.

In a preferred embodiment, a Zero Vascular Reactivity response (ZVR, also Zero Reactivity Curve or ZRC) is defined for a thermal signal using a multivariate model based on physical and physiological characteristics of the measurement site and the surrounding conditions. FIG. 10 illustrates this calculated curve Zero Reactivity Curve (ZRC) 1002 superimposed on a subject's recorded temperature curve (recorded utilizing DTM as discussed above). The recorded temperature curve 1001 shows temperature baseline 1004 and a rebound temperature 1003.

In a preferred embodiment, based on the observed temperature fall in the right index finger (illustrated in FIG. 16) during the cuff occlusion phase and a formula based upon modification to Pennes thermal model of heat transfer, a ZRC is calculated and plotted as the expected temperature rebound curve if the test subject had zero vascular reactivity. In other words, if the blood vessels in the subject's forearm and hand (everything distal to the occluding blood pressure cuff) acted as if they were rigid pipes, then release of the cuff occlusion would result in a temperature rise in the right fingertip that would match the ZRC.

An embodiment of the ZRC formula is as follows:

$$ZRC\left(x_1^{300-2\times(t_{delay})}\right) = F(t_1) + \left\{(\text{Min}_{Temp} - F(t_1)) \times E^{-c \times \frac{37-RoomTemp}{37-F(t_1)} \times x}\right\}$$

The need for ZVR to be defined is that, in certain signal domains such as temperature domain, a zero reactivity signal curve (following administration of a vascular reactivity stimulus, such as cuff occlusion ischemia) is often different than the baseline signal. For example, during digital thermal monitoring of vascular reactivity, the fingertip temperature typically drops during arm cuff occlusion and will rebound following release of the cuff. The characteristics of the rebound curve for zero reactivity is significantly different than the temperature fall curve, and is affected by a number of variables, including room temperature, baseline fingertip temperature prior to cuff occlusion, size of the finger, and air flow surrounding the measurement site.

To accomplish the multivariate model described in this invention, some of the parameters in the Pennes thermal model are measured and others are assumed to be constant. For example, parameters assumed to be constant include airflow, humidity, and heat radiation.

Original Methodology $$\text{term1} = \sum_{i=t1}^{t2}(x_i \times y_i) - \left(\frac{\left(\sum_{t1}^{t2} x_i\right) \times \left(\sum_{t1}^{t2} y_i\right)}{t_2 - t_1}\right) \quad (1)$$

$$\text{term2} = \sum_{i=t1}^{t2}(x_i)^2 - \left(\frac{\left(\sum_{t1}^{t2} x_i\right)^2}{t_2 - t_1}\right) \quad (2)$$

$$\text{slope} = \frac{\text{term1}}{\text{term2}} \quad (3)$$

$$c = \frac{-1 \times \text{slope}}{F(t_1) - \text{RoomTemp}} \quad (4)$$

$$\text{Min}_{Temp} = \min_{t > t_2} F(t) \quad (5)$$

$$t_{min\ temp} = \text{time point for when (Min}_{Temp}\text{) occurs} \quad (6)$$

$$t_{delay} = t_{min\ temp} - 600 \quad (6a)$$

$$ZRC\left(x_1^{300-2\times(t_{delay})}\right) = F(t_1) + \left\{(\text{Min}_{Temp} - F(t_1)) \times e^{-c \times \frac{37-\text{RoomTemp}}{37-F(t_1)} \times x}\right\} \quad (7)$$

$$aRC(x) = F\{(t_2 + 2 \times t_{delay}) \to \text{end}\} - ZRC(x) \quad (8)$$

$$aTR = \max(aRC) \quad (9)$$

Methodology 2: To further reduce variability by adjusting $t_{delay}$. $t_{delay}$ no longer varies when calculating ZRC.

$$\text{term1} = \sum_{i=t1}^{t2}(x_i \times y_i) - \left(\frac{\left(\sum_{t1}^{t2} x_i\right) \times \left(\sum_{t1}^{t2} y_i\right)}{t_2 - t_1}\right) \quad (1)$$

$$\text{term2} = \sum_{i=t1}^{t2}(x_i)^2 - \left(\frac{\left(\sum_{t1}^{t2} x_i\right)^2}{t_2 - t_1}\right) \quad (2)$$

$$\text{slope} = \frac{\text{term1}}{\text{term2}} \quad (3)$$

$$c = \frac{-1 \times \text{slope}}{F(t_1) - \text{RoomTemp}} \quad (4)$$

$$\text{Min}_{Temp} = \min_{t > t_2} F(t) \quad (5)$$

$$t_{min\ temp} = \text{time point for when (Min}_{Temp}\text{) occurs} \quad (6)$$

$$t_{delay} = 0 \quad (6a)$$

-continued $$ZRC\left(x_1^{300-2\times(t_{delay})}\right) = F(t_1) + \left\{(\text{Min}_{Temp} - F(t_1)) \times e^{-c \times \frac{37-\text{RoomTemp}}{37-F(t_1)} \times x}\right\} \quad (7)$$

$$aRC(x) = F\{(t_2 + 2 \times t_{delay}) \to \text{end}\} - ZRC(x) \quad (8)$$

$$aTR = \max(aRC) \quad (9)$$

Methodology 3: To further reduce variability, the 'c' term is adjusted to account for observed (actual) baseline temperature after cuff deflation, instead of using the pre-occlusion temperature value to calculate ZRC. Start temperature is defined as the skin temperature at the fingertip at the beginning of the occlusion phase, when the occluding blood pressure cuff is inflated (which is at the end of the stabilization phase). The Start Temperature has a range of possible values—from a low of room (ambient) temperature of ~22 C to a max of the individual's core body temperature, usually ~37 C. The Start Temperature can vary from one test to another, even when testing the same individual. By calculating a 'c' term, which takes into account both the observed slope of temperature decline during occlusion phase and the RoomTemp, this method helps to adjust the vascular reactivity measurement for patient-specific and room condition-specific variables and will improve the reproducibility of the vascular reactivity measurements.

The 'slope' value used to calculate the 'c' term was varied by inputting various temperature values for '$t_1$' (Start Temperature) in the formulas above.

Slope of Fall Normal Start Temp at Inflation (Original Approach)

slope(1)=((N*n1−(n2a*n2b))/(N*d1−(n2b*n2b)));

$t_1$=F(300)
'Start temperature' using mean(680:740)

slope(2)=(Right_TDef−mean(Ch1(deflatetime+80: deflatetime+140)))/(deflatetime−inflatetime);

$t_1$=F(mean(680:740))
'Start temperature' using mean(720:820)

slope(3)=(Right_TDef−mean(Ch1(deflatetime+120: deflatetime+220)))/(deflatetime−inflatetime);

$t_1$=F(mean(720:820))
'Start temperature' using mean(peak+100)

slope(4)=dfdt(1); % Right_TDef−mean(peak:peak+60);

$t_1$=F(mean(peak+100))
'Start temperature' using (peak+30:peak+60)

slope(5)=dfdt(1); % (Right_TDef−mean(peak+30: peak+60);

$t_1$=F(mean(peak+30:peak+60))
'Start temperature' using (800:900)

slope(6)=(Right_TDef−mean(Ch1(numrows−100: numrows)))/(deflatetime−inflatetime);

$t_1$=F(mean(800:900))
Eventually only slope(3) and slope(6) were found to be more reproducible than slope(1).

Performing a reproducibility study on a set of 8 subjects with multiple tests each allowed determination of the best value for 'Start Temp' by finding the least variable aTR values for the same patient.

In a further embodiment, the main index of vascular reactivity, the aTR (adjusted temperature rebound), is determined as the maximum (peak) difference between the observed temperature rebound curve and the calculated ZRC. This difference is assumed to result from warm blood flow into the forearm/hand that exceeds the amount that had been flowing before the cuff occlusion period. The term to describe this excess blood flow is reactive hyperemia.

FIG. 10 depicts a temperature curve of the right finger 1001 measured by DTM and the corresponding zero reactivity curve ZRC 1002 calculated from the temperature data and formula discussed above. The temperature rebound peak is shown 1003. The area under the rebound curve is compared to the Zero Reactivity Curve 1002.

Figure 11A:
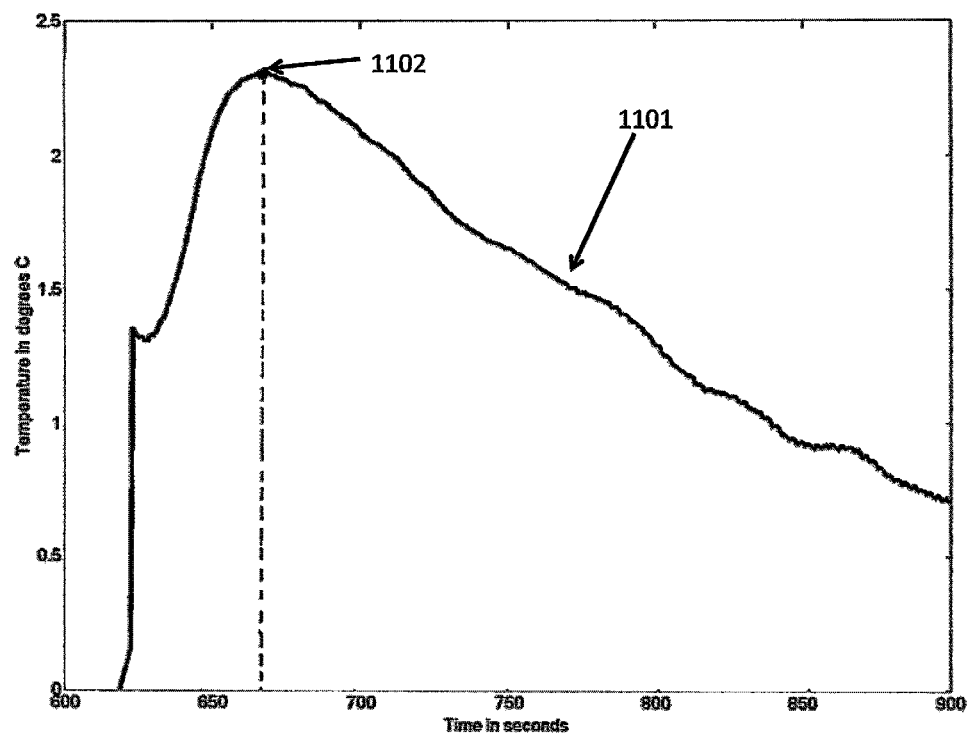
FIG. 11a depicts a reactivity graph. The Reactivity Curve is constructed by subtracting the ZRC curve from the temperature curve of the right finger.

FIG. 11a depicts a reactivity graph. The Reactivity Curve 1101 is constructed by subtracting the ZRC curve from the temperature curve of the right finger during the post occlusion period. Using the reactivity curve 1101, a first type of vascular reactivity index can be determined as the peak, or maximum value 1102, of the Reactivity Curve. This first type of vascular reactivity index is also referred to as the Adjusted Temperature Rebound, or aTR.

Figure 11B:
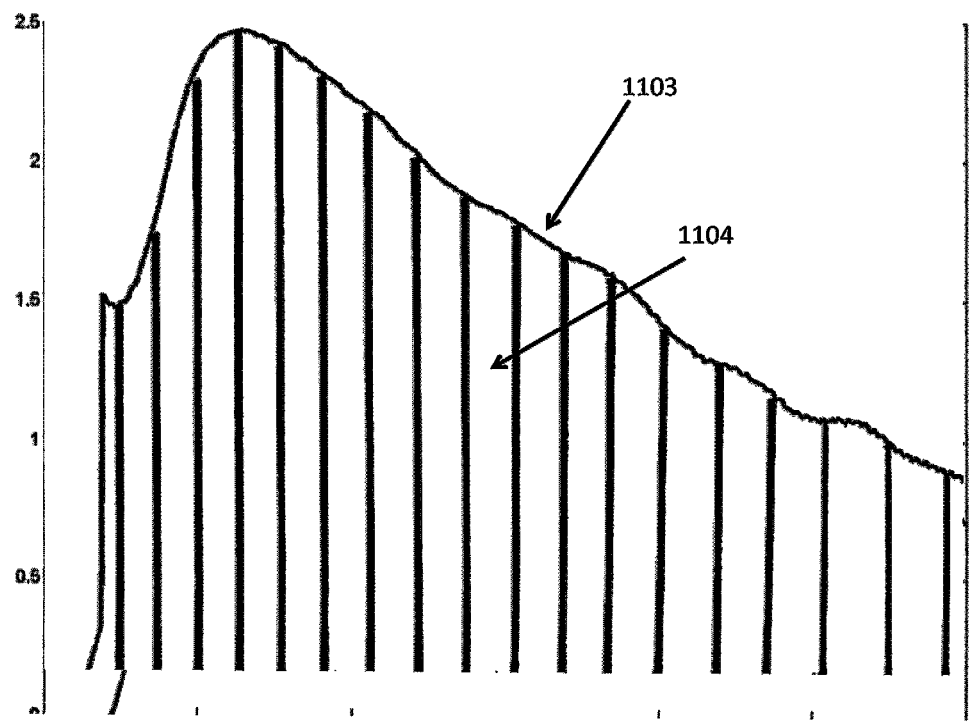
FIG. 11b depicts a reactivity graph. The Reactivity Curve is constructed by subtracting the ZRC curve from the temperature curve of the right finger. Using the reactivity curve, a vascular reactivity index can be determined as the Area Under the Reactivity Curve during a defined time period.

FIG. 11b depicts a reactivity graph. The Reactivity Curve 1103 is constructed by subtracting the ZRC curve from the temperature curve of the right finger. Using the reactivity curve 1103, a second type of vascular reactivity index can be determined as the Area Under the Reactivity Curve 1104 during a defined time period.

Figure 11C:
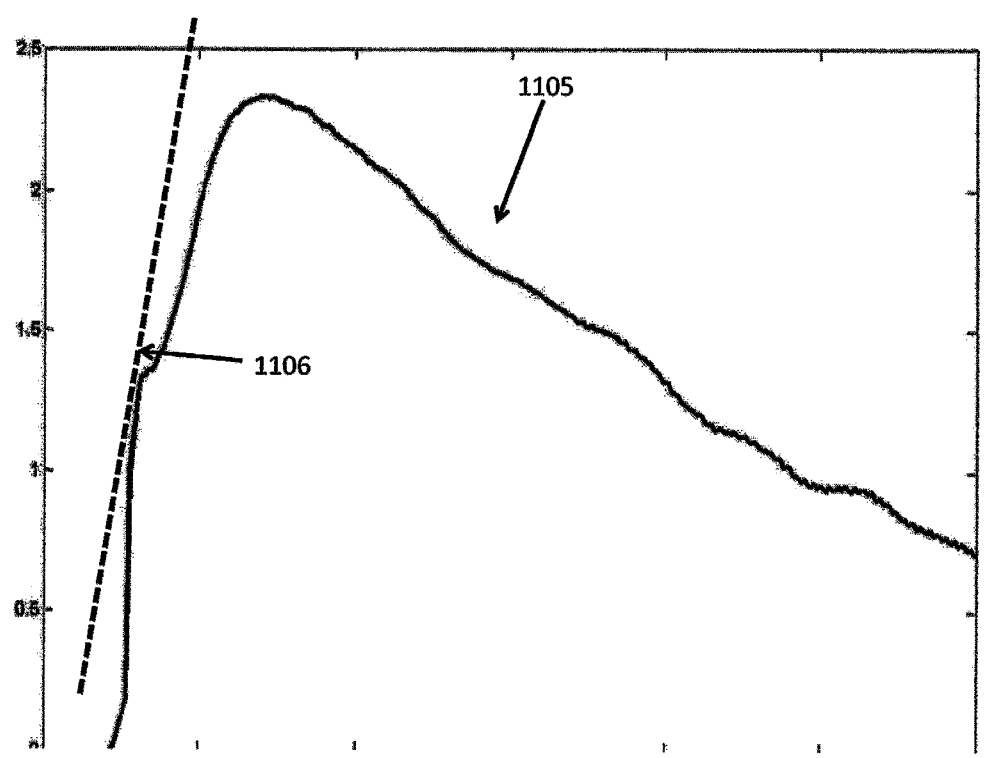
FIG. 11c depicts a reactivity graph. The Reactivity Curve is constructed by subtracting the ZRC curve from the temperature curve of the right finger. Using the reactivity curve, a vascular reactivity index can be determined as the maximum positive slope of the Reactivity Curve.

FIG. 11c depicts a reactivity graph. The Reactivity Curve 1105 is constructed by subtracting the ZRC curve from the temperature curve of the right finger. Using the reactivity curve 1105, a third type of vascular reactivity index can be determined as the maximum positive slope 1106 of the Reactivity Curve.

Figure 12A:
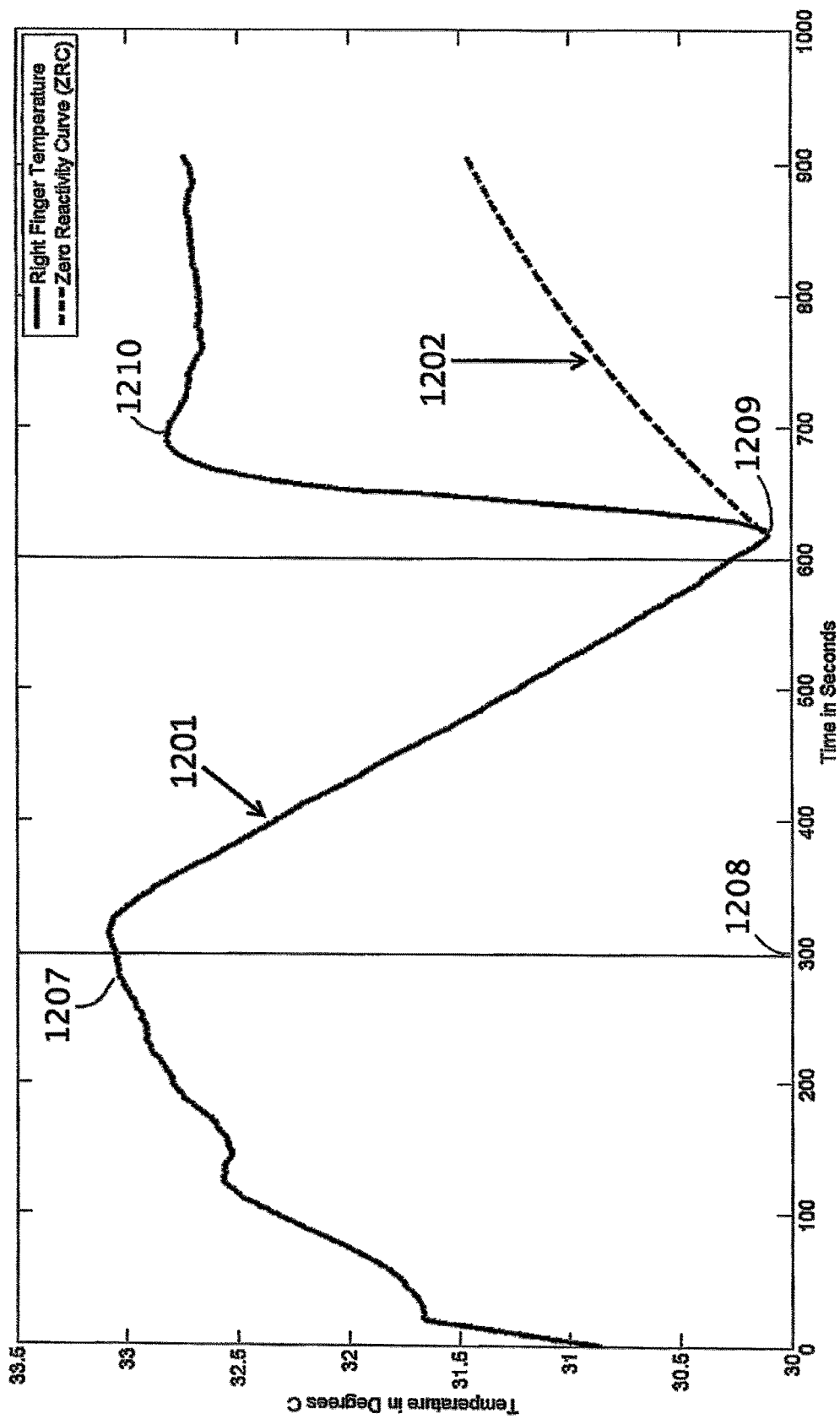
FIG. 12a depicts a temperature curve measured during a vascular reactivity test. The measurement is made from sensors placed proximate to a fingertip of the occluded (right) arm. Also depicted is a Zero Reactivity Curve calculated from the temperature curve.
Figure 12B:
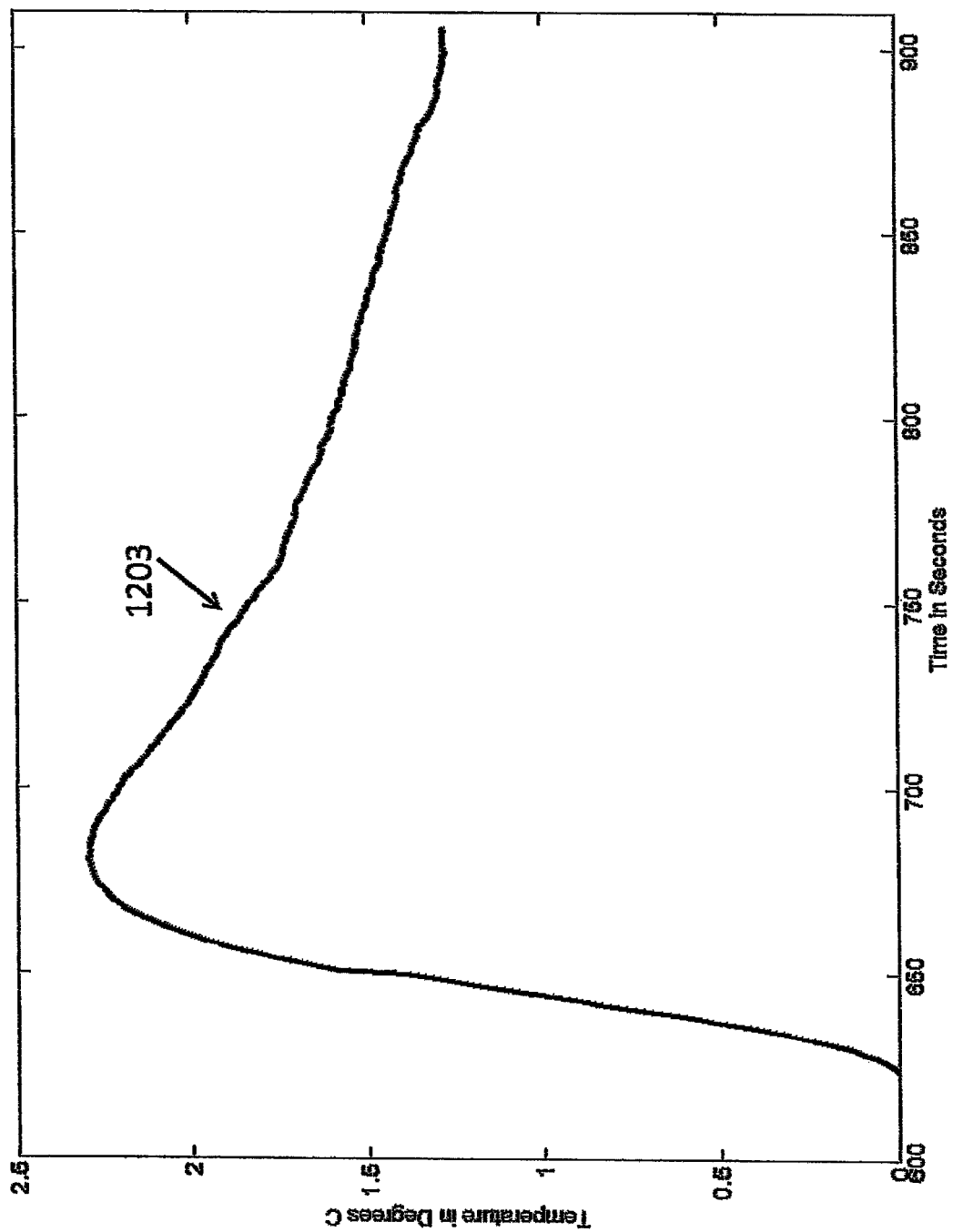
FIG. 12b depicts a reactivity graph utilizing the data of FIG. 12a. The graph represents the difference between the measured temperature curve and the Zero Reactivity Curve.

FIGS. 12a and 12b depict an example of the various temperature curves that are measured or calculated during the administration of a DTM test in which the vascular reactivity index result is considered indicative of "good" vascular reactivity. FIG. 12a depicts one representation of the various temperature curves that are measured throughout the administration of the vascular reactivity test. During the baseline stabilization period 1207, the subject's right fingertip temperature has reached stability and remains very stable. During the right arm cuff occlusion procedure 1208 commencing at time 300 seconds, the right finger temperature falls 1201 toward room temperature due to loss of blood flow. Shortly after the cuff is released at time 600 seconds, the right finger temperature begins to rise 1209 and rapidly rebounds 1210 toward the baseline temperature, rising well above the Zero Reactivity Curve (ZRC) 1202.

FIG. 12b illustrates the calculated vascular reactivity curve 1203. This curve is calculated from the information illustrated in FIG. 12a. The Zero Reactivity Curve 1202 in FIG. 12a is subtracted from the measured value of the temperature curve from the deflate time 1209. The vascular reactivity index is deemed "good" because the vascular reactivity index, determined by taking the maximum value of the reactivity curve, is greater than 2.0

Figure 12C:
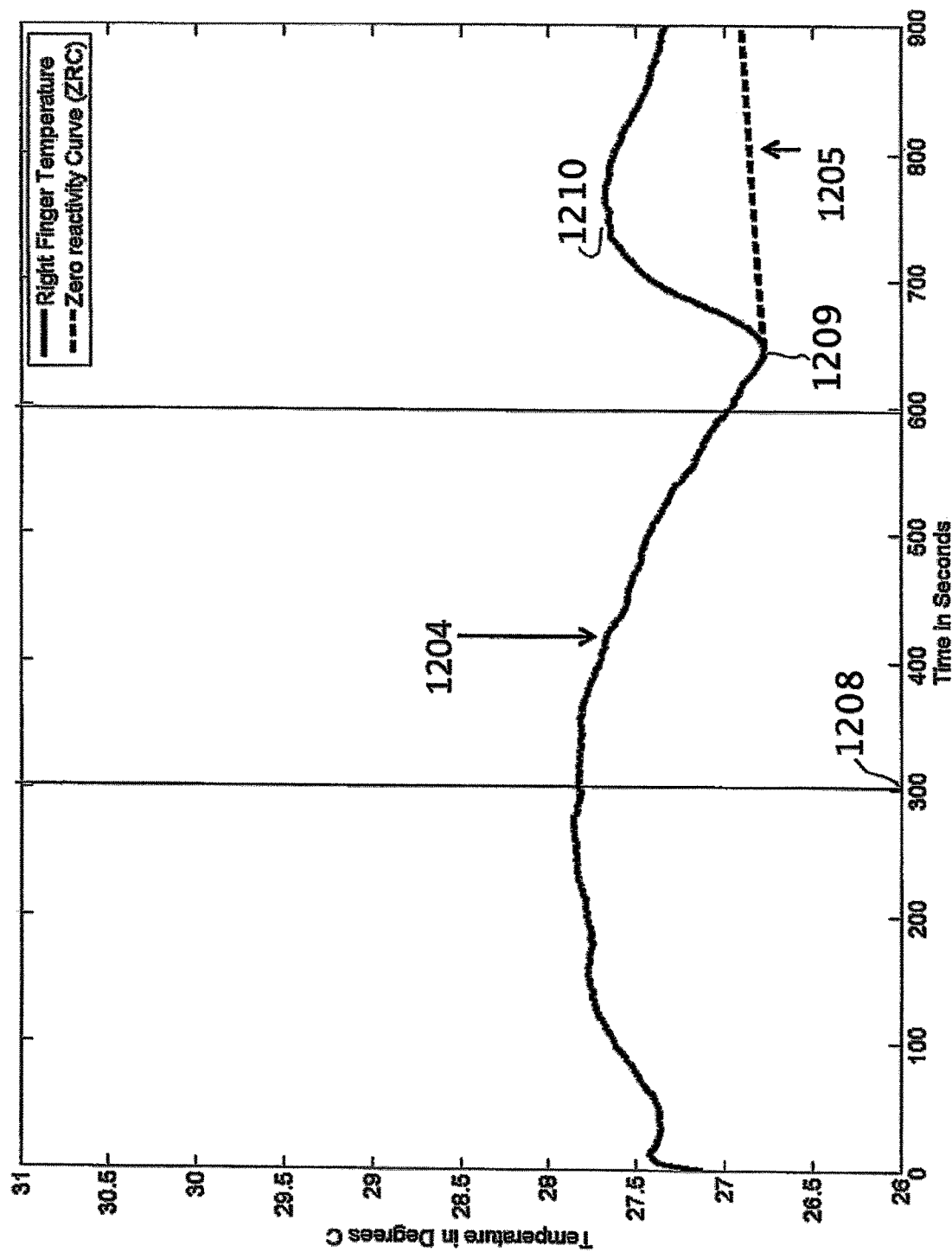
FIG. 12c depicts a right finger temperature curve from the start time through the inflate time and deflate time to the end time. Also shown is a Zero Reactivity Curve calculated from the temperature curve.
Figure 12D:
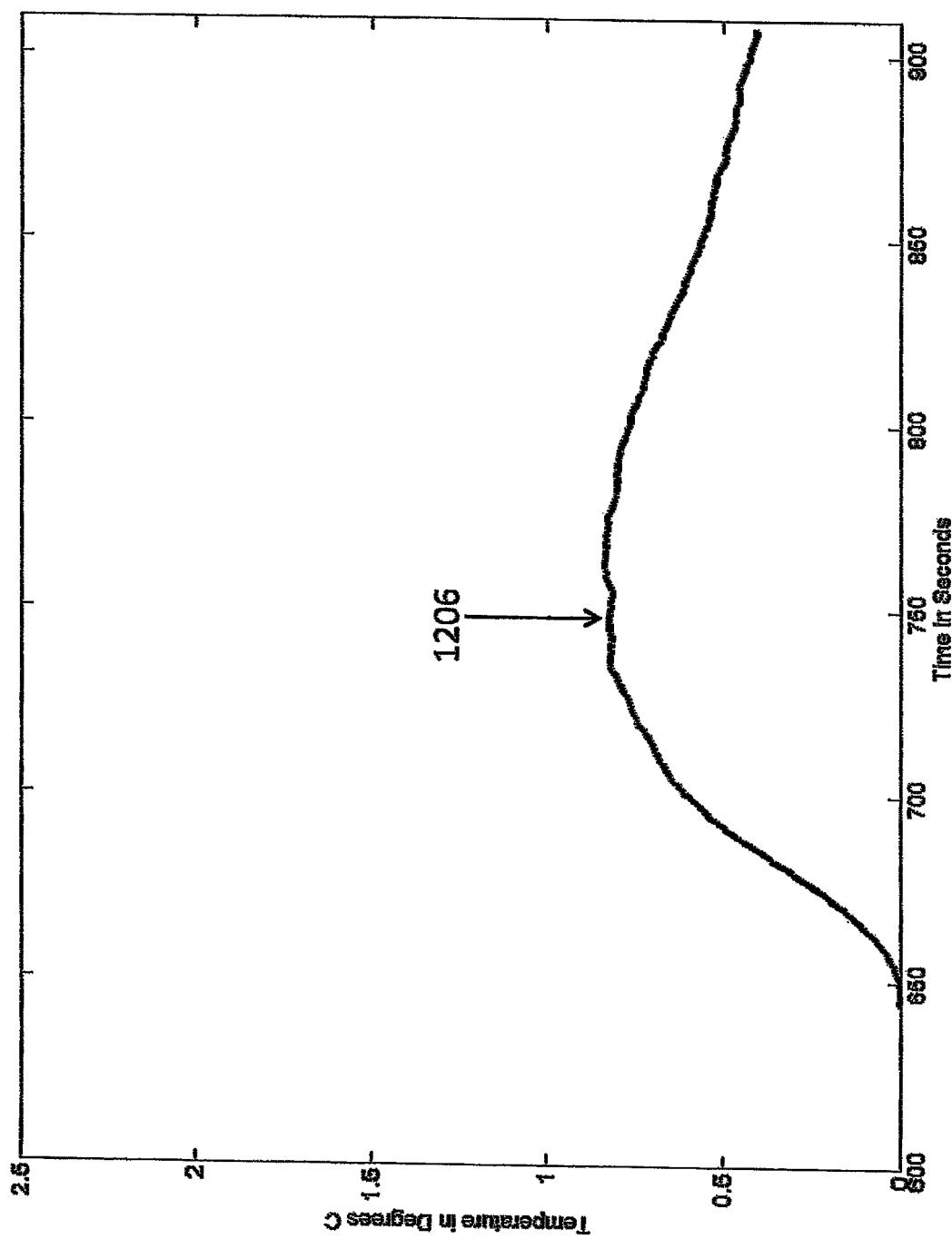
FIG. 12d depicts the reactivity graph calculated from the Zero Reactivity Curve subtracted from the temperature curve illustrated in FIG. 12c.

FIGS. 12c and 12d depict an example of the various temperature curves that are measured or calculated during the administration of a DTM test in which the vascular reactivity index result is considered indicative of "poor" vascular reactivity. FIG. 12c depicts a set of temperature curves for a poor vascular reactivity test. It will be noted that the right finger temperature rebound does not exceed the original stabilization value.

FIG. 12d illustrates the reactivity graph calculated from the temperature curve 1210 of FIG. 12c and the Zero Reactivity Curve 1205. Using the peak value 1206 of the Reactivity Curve, the calculated aTR is less than 1.0, which is considered "Poor" vascular reactivity.

Flag Conditions

This disclosure incorporates several quality control protocols to facilitate the reproducibility and validity of the tests.

Requirements Document: Stability Algorithm: This document contains the requirements for the calculations that the device must perform for the Stabilization Quality Flag and the Sympathetic Response Quality Flag. The algorithm incorporates the following definitions.

inflatetime=Time at which the cuff inflates (in seconds)
deflatetime=Time at which the cuff deflates (in seconds)
endtime=Time at which test ends (in seconds)
starttemp=Temperature of right finger at inflatetime
R=Temperature of Right Finger
L=Temperature of Left Finger
Rm=Room temperature
maxR[t1:t2]=Maximum temperature of right finger from time point #1 to time point #2 (includes time points)
AVG(R[t1:t2])=Average of right finger temperature from time #1 to time #2 (includes time points)
R(inflatetime)=Temperature of right finger at inflatetime
Rm(inflatetime)=Temperature of room at inflatetime.

Stabilization Quality Flag

Any tests that do not exhibit a stable temperature display a 'Baseline Stabilization' flag. All calculations for this flag occur at inflatetime.

Calculate a linear regression of R during inflatetime−180 to inflatetime. The slope of R must be positive and slope and the temperature of right finger at inflatetime must be greater than 27. If this is not true, then calculate the absolute value of the Slope R. The |Slope R| must be less than 0.004 and the temperature of right finger at inflatetime must be greater than 27. If this is not true, then calculate the inflection of R from inflatetime−90 to inflatetime. The inflection must be positive and the temperature of the right finger must be greater than 31.5. If otherwise, flag as 'Baseline Stabilization'.

Sympathetic Response

Calculate start temperature−maxR(inflatetime: inflatetime+120). This value must be less than or equal to one. If the difference is greater than 1, then the data from the left finger must be referenced. Calculate linear regression slope of left finger from deflatetime to endtime. This value must be greater than −0.00167 or the test is Sympathetic Response.

IF starttemp—maxR(deflatetime:deflatetime+120)>1 AND Slope L(deflatetime:endtime)<−0.00167 C/s THEN Sympathetic Response.

Combined DTM and PPG Measurement

This disclosure also teaches a novel and improved method and device evaluating vascular reactivity as an index of vascular health by simultaneously monitoring both macrovascular and microvascular changes in fingertip temperature before, during, and after administration of an arm cuff occlusion ischemia stimulus. This method uses both digital thermal monitoring, or DTM and photoplethysmogram, or PPG. This disclosure also teaches a novel indexing method for both individualized and comparative analysis of cardiovascular health based upon a predicted vascular reactivity curve. This predicted vascular reactivity curve is termed zero reactivity curve or ZRC.

A photoplethysmogram (PPG) is an optically obtained plethysmogram, a volumetric measurement of an organ. A PPG is often obtained by using a pulse oximeter which illuminates the skin and measures changes in light absorption. A conventional pulse oximeter monitors the perfusion of blood to the dermis and subcutaneous tissue of the skin. If the pulse oximeter is attached without compressing the skin, a pressure pulse can also be seen from the venous plexus, as a small secondary peak. Pressure pulse information is contained within the secondary peak.

The change in volume caused by the pressure pulse is detected by illuminating the skin with the light from a light emitting diode (LED) and then measuring the amount of light either transmitted or reflected to a photodiode. Each cardiac cycle appears as a peak, as seen in the figure. Because blood flow to the skin can be modulated by multiple other physiological systems, the PPG can also be used to vascular reactivity to temporary ischemia.

A new technique of processing and analyzing the PPG signals has been developed that closely mimics PAT signals and can serve as a measurement of macrovascular reactivity. PPG technology does not interfere with the temperature measurements and can be easily combined with DTM to produce a single measurement apparatus that could measure both micro- and macro-vascular health at the same time. The advantage of the combination of PPG and DTM provides a single apparatus that can measure both macro- and microvascular health. The combination of the two indices can result in an improvement in the individual predictive value of either of the tests for detection of vascular dysfunction and thereby individuals at risk of a cardiovascular disease.

Figure 15:
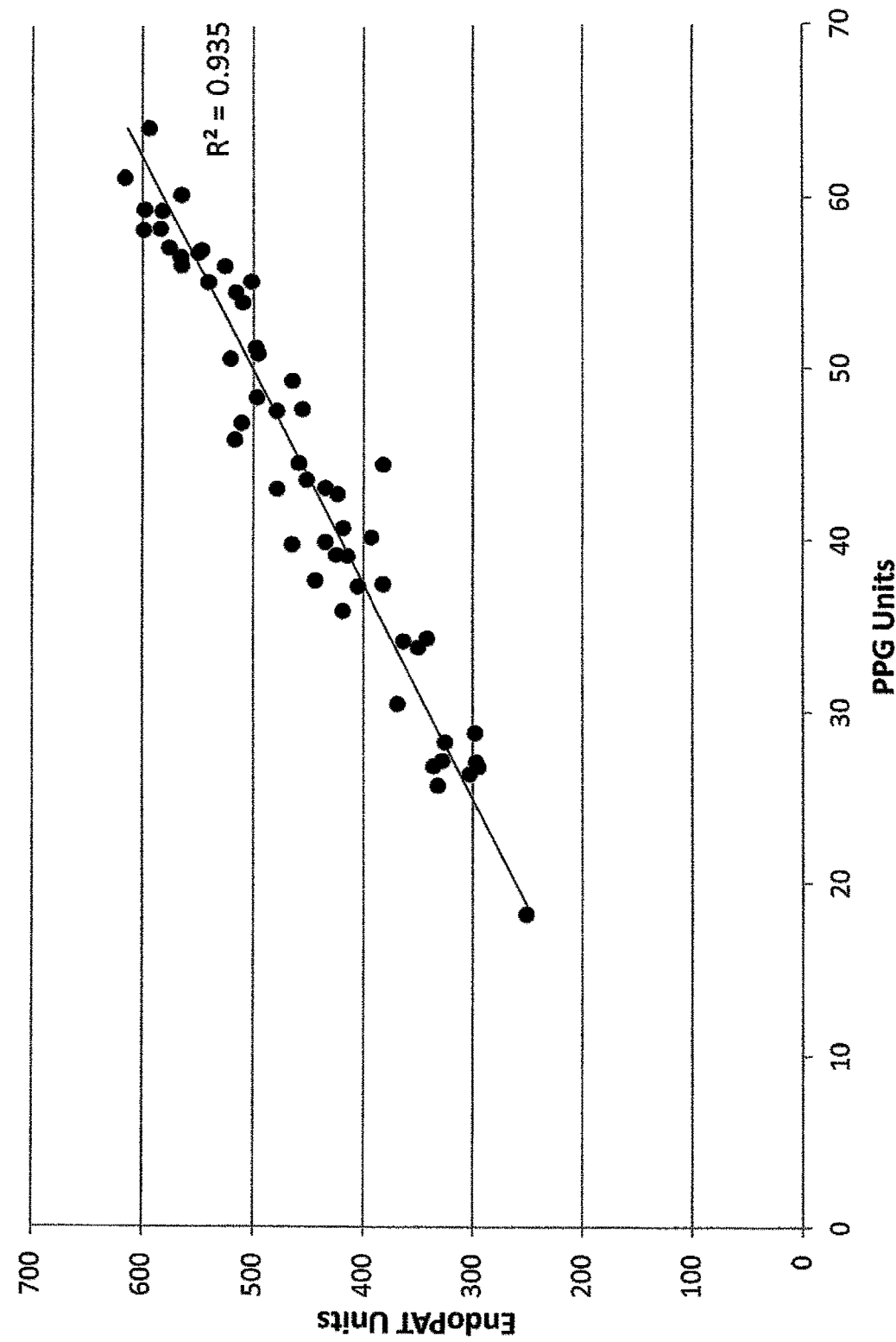
FIG. 15 plots the raw values of the peaks extracted from the data. The peak values show strong a strong correlation with $R^2$ values of up to 0.935.

Consistent with the preceding paragraph, PAT technology requires complete encapsulation of the fingertip and will alter fingertip temperature at the skin level. Due to the nature of the measurement methods, combining both techniques in a single test is not feasible. As illustrated in FIGS. 13, 14 and 15, photoplethysmography PPG provides a good substitute for PAT. When combined with DTM, a system is available that measures macro and microvascular reactivity.

FIG. 13 is a comparison of raw PPG data and raw PAT data in a 1-minute interval. PPG is shown by the top graph 1301 and PAT is shown in the bottom 1302. Both PPG and PAT measure data at a frequency of 128 Hz. This similarity in measurement frequency allows the signals to be aligned and compared at a point-by-point basis. In these graphs, both signals are aligned very closely in the same time frame and have an equal number of data points.

The primary area of comparison is the peak data of both signals 1401, 1402. Using peak data, envelopes of the signals were generated and compared, as seen in FIG. 14. The envelopes of the PPG and EndoPAT signals show remarkable similarity in their behavior. The raw values of the peaks extracted from the data were plotted, as seen in FIG. 15. The peak values show strong a strong correlation with $R^2$ values of up to 0.935.

Based on these findings, photoplethysmography, or PPG can also be used as a measurement of macrovascular reactivity. Since vascular reactivity is dependent on both macro and micro effect, using techniques that incorporate both elements gives greater insight into early disease detection and risk assessment at a clinical level.

Since endothelial function is a systemic property, a localized measurement in a readily accessible location of the human body (such as the digits) can provide an accurate assessment of vascular health in physiologically critical locations such as the coronary arteries. The DTM/PPG subject of this disclosure is a new surrogate for endothelial function monitoring that is non-invasive, operator-independent (observer-independent) and is sufficiently straightforward to be readily implemented across the population to assess individual vascular function. Studies have shown that digit temperature correlates significantly with brachial artery reactivity and thus provides a novel and simple method for assessing endothelial function.

Figure 3:
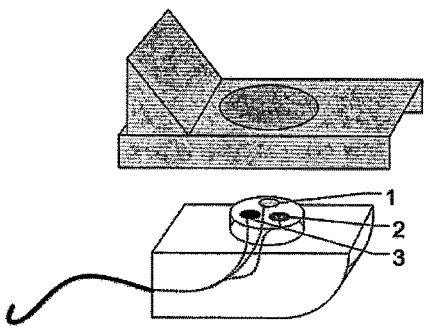
FIG. 3 depicts an embodiment of the finger probe that contains one temperature sensor [1], one reflectance PPG sensor [2], and one single lead ECG sensor [3]. This embodiment could be used to attain pulse wave velocity measurements in addition to ECG, SpO2, and temperature measurement by comparing pulse events in the PPG and ECG signals. This specific design also includes a detachable and disposable probe clip that is used to not only create a physical barrier between the reusable portion of the probe and subjects finger but also as the primary means of attachment to the finger by means of an adhesive surface
Figure 4:
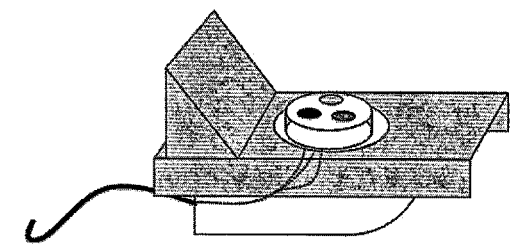
FIG. 4 illustrates the finger probe illustrated in FIG. 3 assembled with the disposable clip.

In the method, a sensitive digital thermal monitoring (DTM) device 1 and light (PPG) device 2, similar to that depicted in FIGS. 3 and 4, is used to measure changes in temperature at the index fingertip of an arm before, during and after brachial artery occlusion (200 mmHg, 2-5 minutes) using a blood pressure cuff. The devices can also be equipped with an ECG sensor 3.

Any skin temperature sensor design suitable for the invention as described herein can be used. For example, FIGS. 8a and 8b and FIGS. 9a and 9b depict suitable designs, among others, for skin sensors.

FIG. 1 depicts an embodiment of the finger probe which houses one temperature sensor 12 and one pulse oximetry sensor 22. The pulse oximeter can be either a transmission or reflectance based probe. This embodiment shows a design that incorporates a transmission probe where the illumination source is located on one side of the probe body and the receiver is located on the opposite side.

Figure 2:
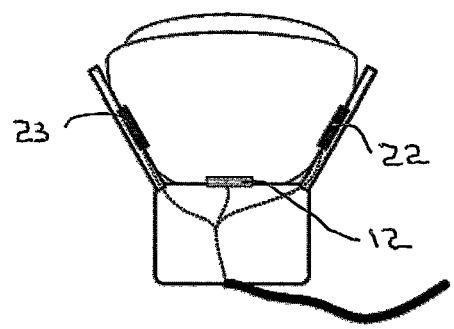
FIG. 2 illustrates the probe placed on a finger. Temperature is measured at the finger pulp and the pulse oximetry readings are attained laterally across the fingertip.

FIG. 2 illustrates the probe placed on a finger. Temperature 12 is measured at the finger pulp and the pulse oximetry 22, 23 readings are attained laterally across the fingertip.

FIG. 3 depicts an embodiment of the finger probe that contains one temperature sensor 1, one reflectance PPG sensor 2, and one single lead ECG sensor 3. This embodiment could be used to attain pulse wave velocity measurements in addition to ECG, SpO2, and temperature measurement by comparing pulse events in the PPG and ECG signals. This specific design also includes a detachable and disposable probe clip that is used to not only create a physical barrier between the reusable portion of the probe and subjects finger but also as the primary means of attachment to the finger by means of an adhesive surface Heart rate variability (HRV) is the physiological phenomenon of variation in the time interval between heartbeats. It is measured by the variation in the beat-to-beat interval. Heart rate variability (HRV) is the physiological phenomenon of variation in the time interval between heartbeats. It is measured by the variation in the beat-to-beat interval. Reduced HRV has been shown to be a predictor of mortality after myocardial infarction although others have shown that the information in HRV relevant to acute myocardial infarction survival is fully contained in the mean heart rate. A range of other outcomes/conditions may also be associated with modified (usually lower) HRV, including congestive heart failure, diabetic neuropathy, depression, post-cardiac transplant, susceptibility to SIDS and poor survival in premature babies.

FIG. 4 illustrates the finger probe illustrated in FIG. 3 assembled with the disposable clip.

Figure 5:
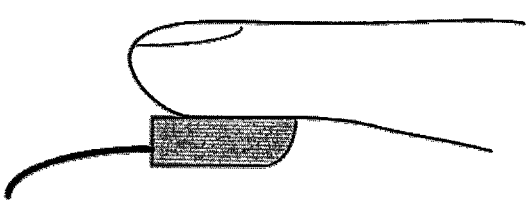
FIG. 5 illustrates a finger positioned on the probe.

FIG. 5 illustrates a finger positioned on the probe.

Figure 6:
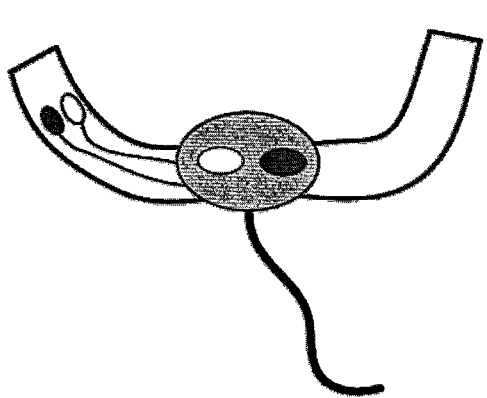
FIG. 6 depicts a flexible embodiment of the finger probe.

FIG. 6 depicts a flexible embodiment of the finger probe.

Figure 7:
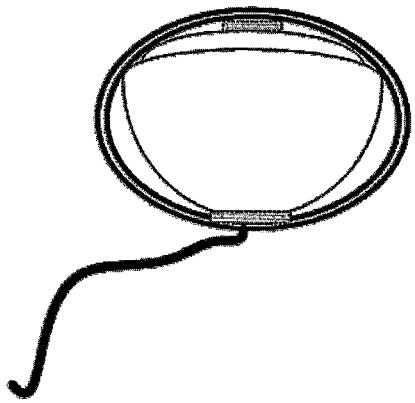
FIG. 7 illustrates the flexible finger probe placed around a subject's finger without regard to the dimensions of the finger. This design makes use of a transmission PPG sensor; however a reflectance PPG probe can also be used.

FIG. 7 illustrates the flexible finger probe placed around a subject's finger without regard to the dimensions of the finger. This design makes use of a transmission PPG sensor; however a reflectance PPG probe can also be used.

Figure 8A:
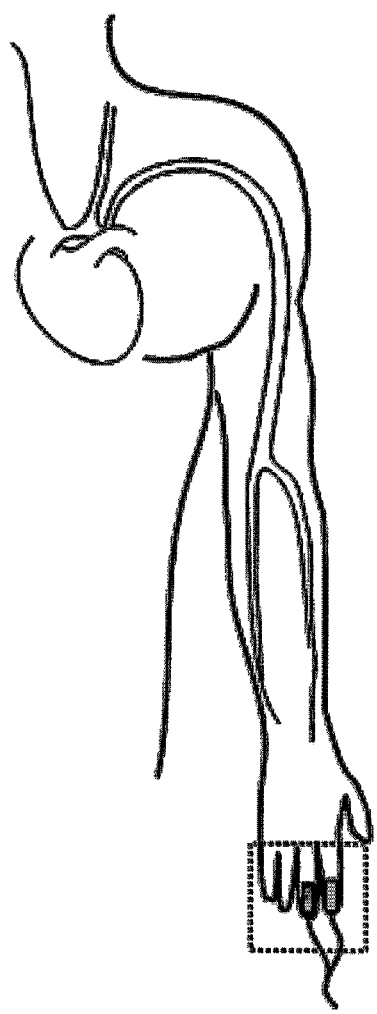
FIG. 8a depicts dual probes positioned on two fingers.

FIG. 8a depicts dual probes positioned on two fingers.

Figure 8B:
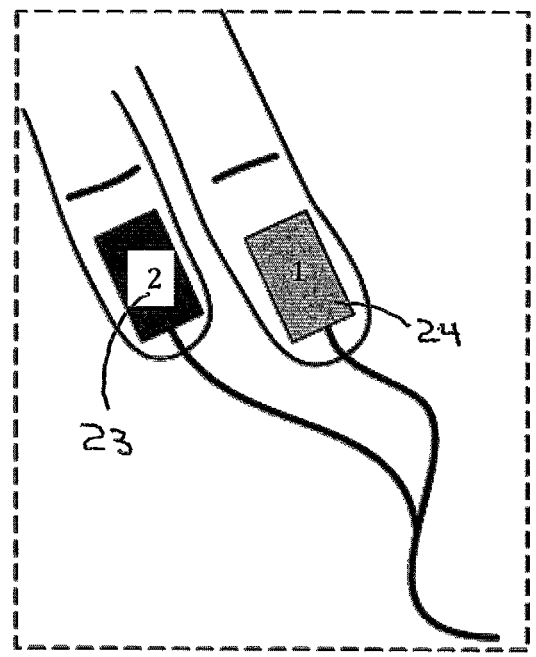
FIG. 8b depicts a method for measuring Pulse Transit Time (PTT) using both a PPG sensor [2] and a single lead ECG sensor [1]. The measurement is made by comparing the time difference in related pulse events in both the ECG and PPG signals.

FIG. 8b depicts a method for measuring Pulse Transit Time (PTT) using both a PPG sensor 23 and a single lead ECG sensor 24. The measurement is made by comparing the time difference in related pulse events in both the ECG and PPG signals.

FIGS. 9a and 9b illustrate the PPG and single lead ECG sensor combined into one sensor.

Figure 30:
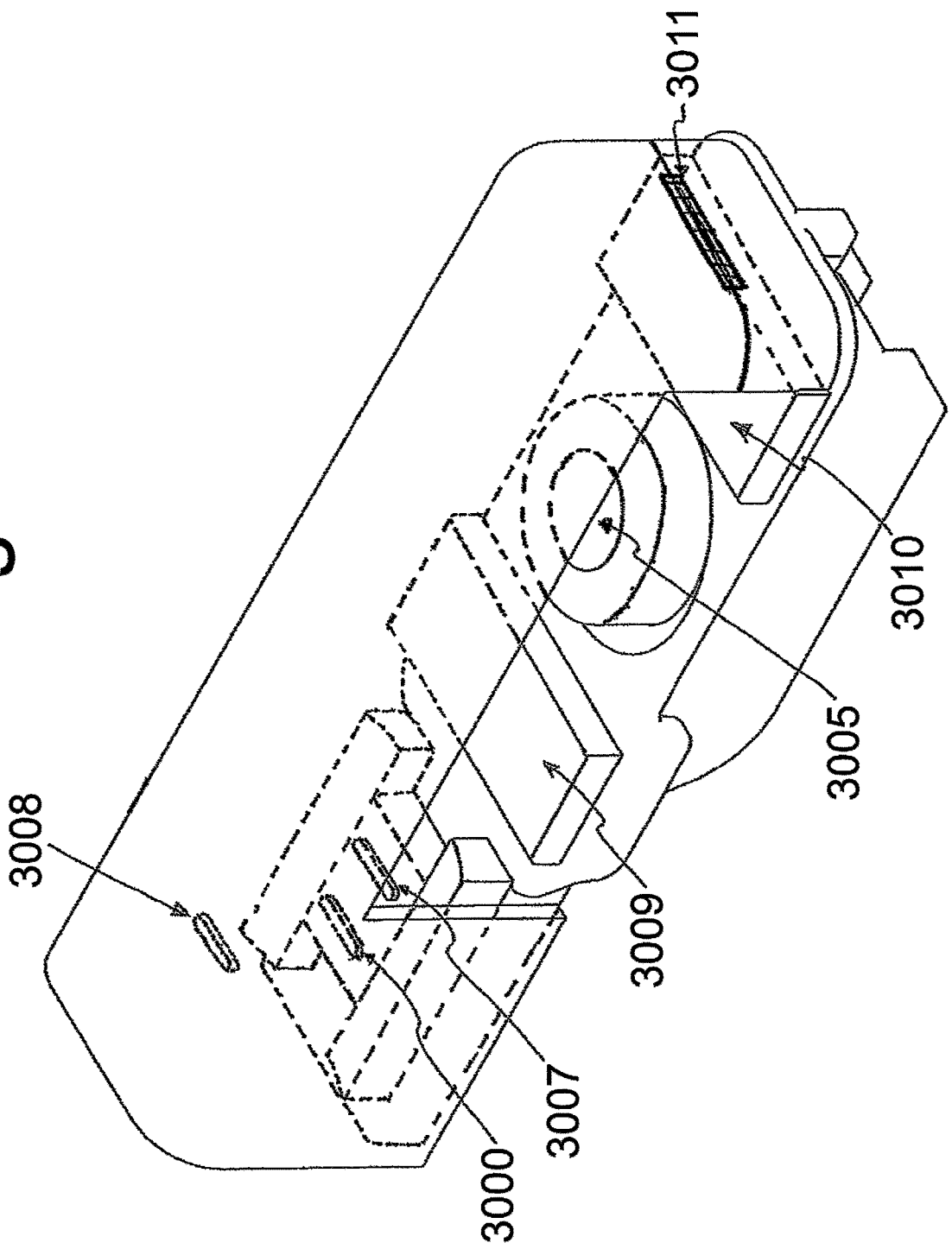
FIG. 30 illustrates a fingertip temperature sensor. Also illustrated is the PPG LED and detector.

Also illustrated is a photoplethysmography—(PPG) sensor. Illustrated is the temperature sensor 2901 in FIG. 30.

Also illustrated is the PPG LED 2902 that emits light which is transmitted off the subject's tissue and detected by the PPG detector 2903. Also illustrated are adhesive pads 2904 to attach the sensor to the subject's fingertip.

Figure 31:
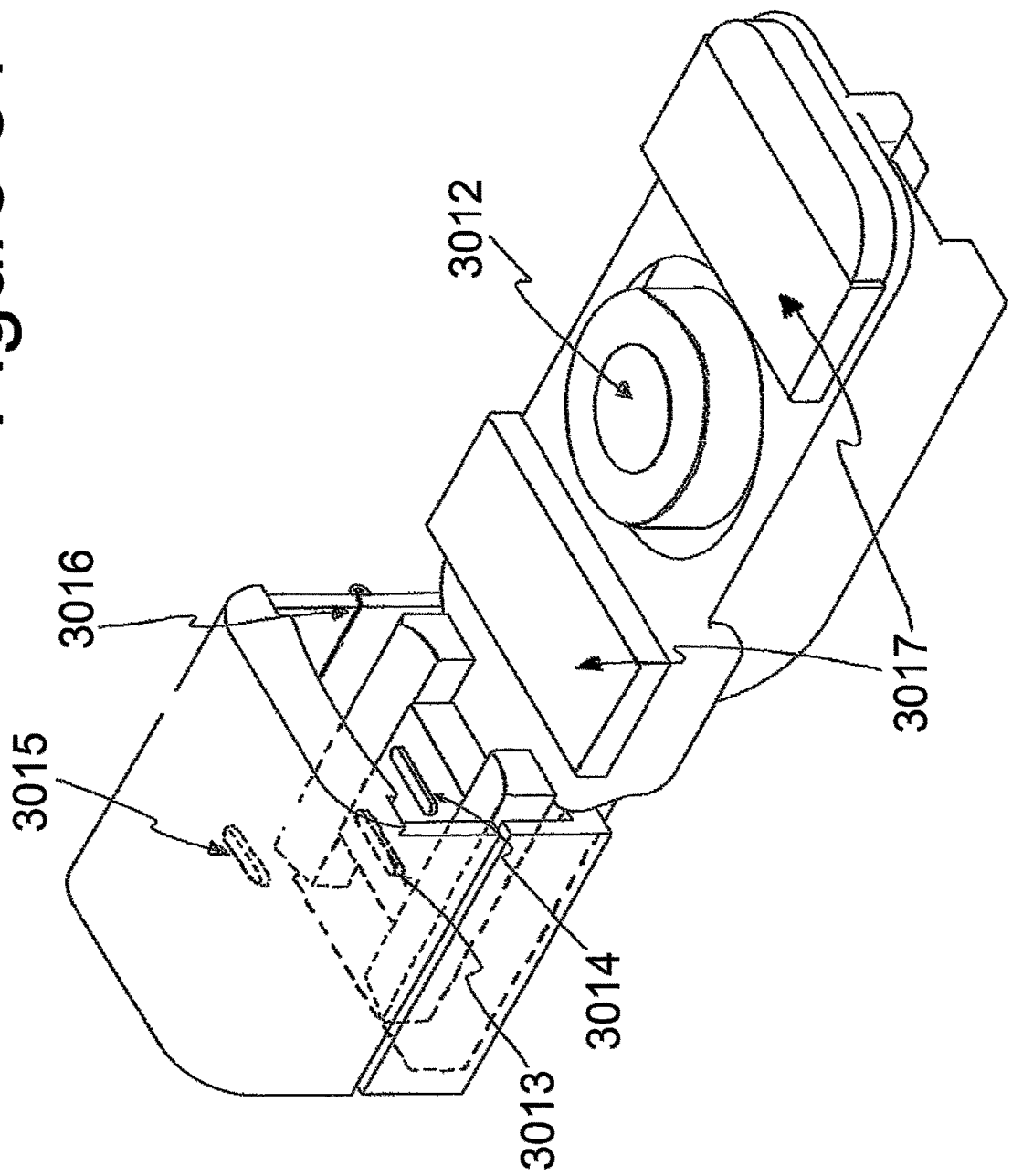
FIG. 31 illustrates another embodiment of a temperature sensor. This sensor also utilizes photoplethysmography sensor. The light emitter and detector are shown. Also a hinge component allowing the upper portion of the sensor to rotate to accommodate the subject's finger.

FIG. 31 illustrates an enclosed sensor. The sensor includes a DTM temperature sensor 3005, and an LED component 3006 and two light detectors; 3007 for reflected light and 3008 for transmitted light. Adhesive pads 3009, 3010 are also illustrated. The enclosing sensor comprises a cover and a hinge positioned at the end of the sensor 3011. The Hinge allows the upper portion to rotate along on the hinge to accommodate a finger. A spring embedded in the hinge creates a small downward force on the upper portion of the probe to prevent excessive movement and to generate a small amount of pressure on a finger inserted into the probe.

FIG. 32 illustrates a partially enclosed sensor. The DTM temperature sensor is shown 3112. Two adhesive pads are also shown 3117. The PPG LED is illustrated 3113. The PPG detectors are illustrated in 3114 for reflected light and in 3115 for transmitted light. A hinge device 3116 encloses the end of the finger tip. A spring embedded in the hinge creates a small downward force on the upper portion of the PPG LED probe to prevent excessive movement and to generate a small amount of pressure on a finger inserted into the probe. It will be appreciated that the PPG data is transmitted to a data acquisition module (not shown) to store the PPG data. The DTM temperature data is also recorded and stored. It will be appreciated that the DTM temperature sensor does not exert pressure on the skin. It also does not heat the skin.

Contralateral Vascular Response (CLVR): Importantly, the present inventors have found that significant temperature changes in control arms were found in some individuals that are thought to reflect the neuroregulatory response to the cuff inflation and deflation. Thus, in one embodiment, measurements on the contralateral hand to that receiving a vascular challenge are used to establish a vascular, metabolic, and neuroregulatory profile for the patient. The present inventors have surprisingly found that, rather than being considered as "noise" to be discounted or controlled, in certain embodiments of the present invention, measurement of skin temperature on the contralateral hand is utilized to provide important insights into the vascular reactivity profile of the individual.

In contrast to the test hand to which a vascular challenge is applied, for example by occlusion of the brachial artery feeding the test hand, the contralateral hand is also monitored for blood flow changes such as by a fingertip temperature measurement on the corresponding digit of the contralateral hand but without vascular challenge to the vasculature feeding the contralateral hand. Since 85% of skin circulation is thermoregulatory and tightly controlled by the sympathetic system, changes in the contralateral finger temperature can be quite diagnostic. In some patients, the contralateral finger temperature goes up in the inflation phase and declines in the deflation phase. The contralateral finger response reflects both the activity of the sympathetic nervous system but also the ability of both the nervous system and the vasculature to work together to respond appropriately to vascular challenge.

Contralateral vasomotion is believed to show the neurogenic factors involved in the arm-cuff based vascular reactivity test and provides, for the first time, the ability to provide characterization of this influence in different individuals.

Physiologic stimuli such as local pain, pressure, and ischemia are known to create systemic effects mostly mediated by autonomic (sympathetic and parasympathetic) nervous system. DTM provides a mechanism to correlate primary and secondary autonomic disorders shown by heart rate variability, and orthostatic hypo and hyper-tension in coronary heart disease and a host of other disorders, with the thermal behavior of contralateral finger.

In one embodiment, the body part is a first hand on the subject, and the contralateral body part is a second hand on the subject. In other embodiments, the body part is a first foot on the subject, and the contralateral body part is a second foot on the subject. In an exemplary embodiment, the body part is a finger on the subject, and the contralateral body part is a toe on the subject.

Changes in blood flow in a contralateral body part as a consequence of a vascular stimulus on a corresponding test body part can be detected by temperature sensing instrumentalities including for example with a thermocouple, thermistor, resistance temperature detector, heat flux detector, liquid crystal sensor, thermopile, or an infrared sensor. However, changes in blood flow in a contralateral body part as a consequence of a vascular stimulus on a corresponding test body part are not limited to temperature detection but may also be detected by skin color, nail capillaroscopy, fingertip plethysmography, oxygen saturation change, laser Doppler, near-infrared spectroscopy measurement, wash-out of induced skin temperature, and peripheral arterial tonometry.

This specification is to be construed as illustrative only and is for the purpose of teaching those skilled in the art the manner of carrying out the invention. It is to be understood that the forms of the invention herein shown and described are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention maybe utilized independently of the use of other features, all as would be apparent to one skilled in the art after having the benefit of this description of the invention.

While specific embodiments have been illustrated and described, numerous modifications are possible without departing from the spirit of the invention, and the scope of protection is only limited by the scope of the accompanying claims.

We claim:

1. A method for assessment of microvascular function, comprising:
   (a) creating a temporary arterial occlusion;
   (b) monitoring skin temperature before, during, and after the arterial occlusion;
   (c) calculating Zero Reactivity Curve (ZRC) based on variables including baseline skin temperature, room temperature, and the observed slope of temperature decline during the arterial occlusion using the following formula $$ZRC[t]=(StartTemp)+(Mintemp-RightStartTemp)*(exp(-1*c*((37-RoomTemp)/(37-RightStartTemp))*t))$$

wherein $c=-dfdt/(StartTemp-RoomTemp)$, wherein StartTemp is baseline temperature of a right finger where the occlusion happens, Mintemp is minimum temperature of the right finger after occlusion, RoomTemp is room temperature, and t is time in seconds after minimum temperature of the right finger after occlusion; and (d) assessing microvascular function based on comparing the observed temperature rebound after the occlusion and the Zero Reactivity Curve.

2. A method for simultaneous assessment of microvascular function and macrovascular function using a skin temperature sensor and a photoplethysmography (PPG) sensor, comprising:
   (a) creating a temporary arterial occlusion;
   (b) measuring skin temperature and PPG signals before, during, and after the arterial occlusion;
   (c) calculating Zero Reactivity Curve (ZRC) based on variables including baseline skin temperature decline during the arterial occlusion according to below formula:

$$ZRC[t]=(StartTemp)+(Mintemp-RightStartTemp)*(exp(-1*c*((37-RoomTemp)/(37-RightStartTemp))*t))$$

wherein $c=-dfdt/(StartTemp-RoomTemp)$, wherein StartTemp is baseline temperature of a right finger where the occlusion happens, Mintemp is minimum temperature of the right finger after occlusion, RoomTemp is room temperature, and t is time in seconds after minimum temperature of the right finger after occlusion;
   (d) calculating peak-to-base amplitude, peak-to-trough amplitude, pulse waveform analysis, area under the curve analysis, reflectance waveform analysis, or a combination thereof from the PPG signals;
   (e) assessing microvascular function based on comparing observed temperature rebound after the occlusion and the ZRC; and
   (f) accessing macrovascular function based on comparing peak-to-base amplitude, peak-to-trough amplitude, pulse waveform analysis, area under the curve analysis, reflectance waveform analysis, or a combination thereof from the PPG signals, before and after the arterial occlusion.

3. The method of claim 2 further comprising: obtaining an electrocardiography (ECG) signal using an electrocardiography sensor for enabling cardiac function assessment in addition to vascular in addition to micro and macro vascular function assessments.

4. A method of claim 3 further comprising: of calculating pulse wave velocity by comparing pulse events in PPG and ECG signals, and calculating heart rate variability by using PPG signals.

* * * * *